(12) United States Patent
Barnea

(10) Patent No.: US 7,495,071 B2
(45) Date of Patent: Feb. 24, 2009

(54) ANTIPROLIFERATIVE PEPTIDES AND ANTIBODIES FOR THEIR DETECTION

(75) Inventor: Eytan R. Barnea, Cherry Hill, NJ (US)

(73) Assignee: BioSpectrum, Inc., Cherry Hill, NJ (US)

( * ) Notice: Subject to any disclaimer, the term of this patent is extended or adjusted under 35 U.S.C. 154(b) by 0 days.

(21) Appl. No.: 11/181,331

(22) Filed: Jul. 14, 2005

(65) Prior Publication Data

US 2007/0185023 A1    Aug. 9, 2007

Related U.S. Application Data

(60) Provisional application No. 60/587,919, filed on Jul. 14, 2004.

(51) Int. Cl.
C07K 16/00 (2006.01)
A61K 38/00 (2006.01)

(52) U.S. Cl. .................. 530/327; 530/328; 530/329

(58) Field of Classification Search .............. None
See application file for complete search history.

(56) References Cited

U.S. PATENT DOCUMENTS

| | | | |
|---|---|---|---|
| 5,648,340 A | | 7/1997 | Barnea |
| 5,665,355 A | * | 9/1997 | Primi ................ 424/140.1 |
| 6,225,097 B1 | * | 5/2001 | Obata et al. ............. 435/183 |
| 6,365,727 B1 | | 4/2002 | Yoon et al. |
| 2003/0109690 A1 | | 6/2003 | Ruben et al. |
| 2003/0203410 A1 | | 10/2003 | Barnea |

FOREIGN PATENT DOCUMENTS

| | | |
|---|---|---|
| DE | 4400640 A1 | 7/1995 |
| WO | WO 92/09294 | 6/1992 |
| WO | WO 00/01402 A1 | 1/2000 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Skolnick et al. (Trends in Biotech., 18(1):34-39, 2000).*
Chakrabarti et al Nature vol. 328 p. 543 (1987).*
Matsuyama et al. Biol. Chem. vol. 263 p. 1712 (1988).*
Barnea, The first three months of pregnancy, 1991, In Teoh, E.S. and Ratnam, S.S. (eds.) The Future of Obstetrics and Gynecology, FIGO pp. 17-36, Carnforth: Parthenon Publishers.
Barnea et al., The First Twelve Weeks of Gestation: A New Frontier in Investigation and Intervention, 1992, Editorial Position, Berlin: Springer-Verlag.
Barnea et al., Endocrinology of the placental and embryo-placental interaction, 1992. In Barnea et al. (eds), The First Twelve Weeks of Gestation, pp. 128-153, Berlin: Springer-Verlag.
Barnea et al., Epilogue, 1992. In Barnea et al. (eds), The First Twelve Weeks of Gestation, pp. 542-548, Berlin: Springer-Verlag.
Barnea et al. (eds), Implantation and Early Pregnancy in Humans, 1994, Editorial Position, Carnforth: Parthenon Publishing.
Barnea, Dual effects of embryo-derived factors on hCG secretion by placental explants, 1994. In Barnea et al. (eds), Implantation and Early Pregnancy in Humans, pp. 271-282, Carnforth: Parthenon Publishing.
Fernandez et al., Cancer and pregnancy:Clinical management and biological analyogy, 1994. In Barnea et al. (eds), Implantation and Early Pregnancy in Humans, pp. 355-377, Carnforth: Parthenon Publishing.
Barnea, (Editor-in-Chief), 1995-present, Early Pregnancy: Biology & Medicine.
Barnea, (Keynote Editorial), 1995, New Frontiers in early pregnancy investigation, Early Preg: Biol & Med. 1: 1-3.
Barnea, (Editorial), 1995, EnVision the Field of Early Pregnancy Investigation, Early Preg: Biol & Med. 1: 169-170.
Barnea et al., (Editorial), 1996, Reflections on early pregnancy: organizing chaos or organized chaos? Early Preg. Biol & Med. 2: 77-79.
Jauniaux et al., Embryonic Medicine and Therapy, 1997, Editorial Position, Oxford: Oxford University Press.
Jauniaux et al., Preface: Future Directions and Limitations, 1997. In Jauniaux et al. (eds), Embryonic Medicine and Therapy, pp. 7-8, Oxford: Oxford University Press.
Barnea et al., The Embryo/Trophoblast Paradox, 1997. In Jauniaux et al. (eds), Embryonic Medicine and Therapy, pp. 256-279, Oxford: Oxford University Press.
Barnea, (Editorial), 1997, The Embryo: a privileged entity in a privileged site: Lessons learnt from embryonal development. Early Preg: Biol & Med. 3: 77-80.
Rayburn, (Jauniaux et al. eds), Embryonic Medicine and Therapy, 1999, New England J. of Med. Book Review: 340(19): 1519.
Barnea et al., Maternal Immune Response to Trophoblast, GTD, and Cancer, 2000, Shoenfeld et al. (eds). In Cancer and Autoimmunity, pp. 343-350, Elsevier Science: B.V. Publishers.
Barnea et al. (eds), Cancer and Pregnancy, 2001, Editorial Position, Springer: London.
Barnea et al., Pregnancy Derived Compounds that Control Proliferation, 2001. In Cancer and Pregnancy, Barnea et al. (eds), pp. 274-284 Springer: London.
Barnea, Epilogue: Cancer and Pregnancy-a reason for hope, 2001. In Cancer and Pregnancy, Barnea et al. (eds), pp. 296-298, Springer: London.
Barnea et al., Embryo-maternal signaling prior to implantation, 2001. In Obstetrics & Gynecology, Section 2 Human Reproduction-Anatomy, Physiology, Embryology, pp. 112-117, Munteanu Ed., Romanian Academy of Sciences Publishers.
Barnea et al., Implantation in Obstetrics & Gynecology, Section 2 Human Reproduction-Anatomy, Physiology, Embryology, 2001, pp. 117-123, Munteanu Ed., Romanian Academy of Science Publishers.

(Continued)

*Primary Examiner*—Sheela J Huff
(74) *Attorney, Agent, or Firm*—Pepper Hamilton LLP

(57) ABSTRACT

The present invention relates to developmental peptides and peptidomimetics thereof, which may be used therapeutically to inhibit abnormal cell proliferation of damaged cells, including cancer cells or virally infected cells. In one embodiment, a seven to eleven amino acid developmental peptide and methods of using the same is provided.

13 Claims, 8 Drawing Sheets
(3 of 8 Drawing Sheet(s) Filed in Color)

OTHER PUBLICATIONS

Barnea et al., Evolution of the feto-placental unit, 2001. In Obstetrics & Gynecology, Section 2 Human Reproduction-Anatomy, Physiology, Embryology, pp. 170-175, I. Munteanu Ed, Romanian Academy of Science Publishers.

Barnea et al., Immune System (IS) and Proliferation Control (PC) from Embryo to Adulthood: Roles of Preimplantation Factor (PIF) and of Developmental Proteins (DPs), 2001. In The Woman and Child Before, During and After Pregnancy, E.V. Cosmi Ed (Monduzzi Editore).

Mirhashemi, (Barnea et al. eds), Cancer and Pregnancy, 2002, New England J. of Med. Book Review 346(24): 1921.

Barnea et al., Human embryonal extracts modulate placental function in the first trimester: Effects of visceral tissues upon chorionic gonadotropin and progesterone secretion, 1989, Placenta 10: 331-334.

Shurtz-Swirski et al., Human Embryo modulates placental function in the first trimester: Effects of neural tissues upon chorionic gonadotropin and progesterone secretion, 1991, Placenta 12: 521-531.

Shurtz-Swirski et al., Patterns of secretion of human chorionic gonadotropin by superfused placental explants and the embryo-placental relationship following maternal use of medications, 1992, Hum. Reprod. 7: 300-304.

Barnea et al., Control of cell proliferation by embryonal-origin factors, 1996, Am. J. Reprod. Immunol. 35: 318-324.

Barnea et al., Nouvelles perspectives de prevention des dommages de l'environnement sur l'embryon (New perspectives on prevention of environmentally-induced damage to the embryo), 1996, Reproduction Humaines et Hormones 7: 423-428.

Barnea et al., Human embryo regulates placental function in first trimester, 1988, International Congress of Endocrinology, Kyoto, Japan (Abstract).

Morgan et al., Approaches to the Discovery of Non-Peptide Ligands for Peptide Receptors and Peptidases, 1989, Annual Reports in Medicinal Chemistry 24: 243-252.

Ripka et al., Peptidomimetic design, 1998, Current Opinion in Chemical Biology 2:441-452.

Hruby et al., Synthesis of oligopeptide and peptidomimetic libraries, 1997, Current Opinion in Chemical Biology 1:114-119.

Hruby et al., Conformational and Topographical Considerations in Designing Agonist Peptidomimetics from Peptide Leads, 2000, Current Medicinal Chemistry 7:945-970.

Remington's Pharmaceutical Sciences, 1990, 18th ed., Mack Publishing, Easton, PA (TOC).

Rayburn, (Jauniaux et al. eds), Embryonic Medicine and Therapy, 1999, New England J. of Med. Book Review: 340(19): 1519, cover only.

Barnea et al., Maternal Immune Response to Trophoblast, GTD, and Cancer, 2000, Shoenfeld et al. (eds). In Cancer and Autoimmunity, Elsevier Science: B.V. Publishers, p. 309-316.

Barnea et al. (eds), Cancer and Pregnancy, 2001, Editorial Position, Springer: London, table of contents only.

Barnea et al., Pregnancy Derived Compounds that Control Proliferation, 2001. In Cancer and Pregnancy, Barnea et al. (eds), Springer: London, p. 275-284.

Barnea et al., Implantation in Obstetrics & Gynecology, Section 2 Human Reproduction-Anatomy, Physiology, Embryology, 2001, Munteanu Ed., Romanian Academy of Sciences Publishers, table of contents only.

Barnea et al., Immune System (IS) and Proliferation Control (PC) from Embryo to Adulthood: Roles of Preimplantation Factor (PIF) and of Development Proteins (DPs), 2001. In The Woman and Child Before, During and After Pregnancy, E.V. Cosmi Ed (Monduzzi Editore), p. 93-102.

Mirhashemi, (Barnea et al. eds), Cancer and Pregnancy, 2002, New England J. of Med. Book Review 346(24): 1921, (abst).

Barnea et al., Human embryonal extracts modulate placental function in the first trimester: Effects of visceral tissues upon chorionic gonadotropin and progesterone secretion, 1989, Placenta 10: 331 344.

Barnea, (Editor-in-Chief), 1995, Early Pregnancy: Biology & Medicine cover page only.

Jauniaux et al., Embryonic Medicine and Therapy, 1997, Editorial Position, Oxford: Oxford University Press, Table of Contents only.

* cited by examiner

AMINO ACID SEQUENCE and PARTIAL HOMOLOGY of DP peptide

| Sequence | Sequence Matching |
|---|---|
| [H]-i-e-v-l-g-k-r-i-k-g-t-[OH] | -100% match with 11 a.a. (Simian Immunodeficiency Virus pol polyprotein) |
| [H]-i-d-v-l-g-k-r-i-k-g-t-[OH] | -90% match with 11 a.a. (Simian Immunodeficiency Virus pol polyprotein)<br>-100% match with 7 a.a. (Human immunoglobulin lambda chain) |
| [H]-i-r-v-l-g-k-r-i-k-g-t-[OH] | -90% match with 11 a.a. (Simian Immunodeficiency Virus pol polyprotein) |
| [H]-i-e-v-t-g-k-r-i-k-g-t-[OH] | -90% match with 11 a.a. (Simian Immunodeficiency Virus pol polyprotein) |
| [H]-i-d-v-t-g-k-r-i-k-g-t-[OH] | -81% match with 11 a.a. (Simian Immunodeficiency Virus pol polyprotein) |
| [H]-i-r-v-t-g-k-r-i-k-g-t-[OH] | -100% match with 7 a.a. (Simian Immunodeficiency Virus pol polyprotein)<br>-100% match with 7 a.a. (Simian Immunodeficiency Virus protease, Chain A) |

FIG. 5

ANTIPROLIFERATIVE PEPTIDES AND ANTIBODIES FOR THEIR DETECTION

CLAIM OF PRIORITY

This application claims priority to U.S. Provisional Application No. 60/587,919 filed Jul. 14, 2004 titled "Antiproliferative Peptides and Antibodies for their Detection", the contents of which are incorporated herein by reference.

BACKGROUND OF THE INVENTION

The present invention relates to peptides and peptidomimetics, which may be used therapeutically to inhibit abnormal cell proliferation. It is based at least in part, on the discovery of a class of developmental peptides or proteins (DPs) isolated from embryonic tissues which have been found to exhibit antiproliferative effects on a variety of damaged cells ranging from pre-cancerous to resistant cancer cells and virally infected cells. Developmental peptides and molecules that mimic the structure and function of these peptides are capable of inhibiting abnormal cell proliferation.

In addition, the present invention relates to specific antibodies generated against developmental peptides and their functional equivalents, their use to determine the peptide expression in various normal and pathologic tissues and biological fluids, and their use as biomarkers specifically but not limited to cancer. The present invention further investigates the use of these antibodies for isolating and characterizing additional developmental peptides exhibiting antiproliferative action that may share homology to developmental peptides described herein.

The present invention relates to developmental peptides and peptidomimetics which exert antiproliferative effects. The developmental peptides antiproliferative effects may be attributed to their ability to control the delicate balance between proliferative and antiproliferative factors in developing tissues within the embryo, and actually continuing such function throughout adulthood. Developmental peptides may further have a similar antiproliferative homeostatic role in the adult, preventing abnormal proliferation, such as it occurs in cancer.

The discovery is based on the theory that pregnancy can be viewed as a reversible form of cancer. In that context, embryonal cells are rapidly proliferating, migrating, and invading the maternal body. In contrast to cancer cells, the embryonal cells undergo differentiation, give rise to organ development and to a major shift from structure to function leading to the birth of an individual. In the case of cancer, altered cell proliferation leads in general to disrupted function and consequently to the demise of the individual, unless the cancer is aggressively controlled and eradicated. An additional aspect of pregnancy is that of maternal immune tolerance, which is a reversible phenomenon and conditional in general on the health of the conceptus. In contrast, frequently, the presence of cancer is associated with immune suppression and altered immune response.

As described in U.S. Pat. No. 5,648,340 entitled "Gestational agents for controlling cell proliferation" filed Jan. 17, 1995 and PCT Application No. PCT/US91/08046 filed Oct. 31, 1991, entitled "Proteins Purified from Mammalian Gestational Tissue which Controls Cell Proliferation" incorporated herein by reference, developmental peptide agents have been broadly identified to operate by controlling the development of the embryo such that proliferation, placental invasivity and differentiation may occur without substantially injuring the maternal host. U.S. Pat. No. 5,648,340 discloses the purification of protein extracts having a molecular weight less than 10,000 (and particularly less than 8,000 daltons) which have antiproliferative activity and other agents of less than 3,000 daltons, which oppositely exhibit proliferative activity. The protein preparations described therein are described as high molecular weight extracts effective against a wide variety of viruses, as well as isolation and sequencing of a low molecular weight seven amino acid set of peptides which exert antiproliferative effects. In U.S. application Ser. No. 10/117,728 filed Apr. 4, 2002 entitled "Gestational agents which modulate cell proliferation," the profound and multitargeted effects of high molecular weight developmental peptides on cancer cells proliferation is described. Developmental peptides inhibited tumor promoters and promoted tumor inhibitors acting on both cell cycle and cell cycle independent intracellular proteins, with minimal effect exerted on normal white blood cells. Overall effect of developmental peptides appeared to be exerted at the G0-G1 transition phase. On MCF7 cells (estrogen receptor positive breast cancer cells), P53 phosphorylation increased while pRb decreased, mdm2 separated from p53, and later p21 was induced. Cyclin D1 and E were blocked, MAPkinase temporarily dephosphorylated, Bcl2 was blocked while BAD increased.

The present invention relates to the further isolation and characterization of several developmental peptides as well as sequencing of such peptides, for example, from mammalian adult liver, and documenting their presence in a native form also within the porcine embryonal liver. In addition, generation of synthetic developmental peptides and peptidomimetics and testing of their activity against cancer cells and virally infected cells and the mechanism of developmental peptide action is further described. Further, the present invention relates to the use of developmental peptides and KLH as carrier for the generation of polyclonal antibody in chicken (IgY) and determining the expression of the proteins and peptides that contain a conserved seven to eleven amino acid sequence in a variety of embryonal and adult tissues.

The identification of developmental peptides in both fetal and adult tissues and their highly preferential expression in normal epithelium point to their important biological role in rapidly replicating cells where negative regulators are likely to have a significant role in assuring proper control of proliferation. Also their expression in highly proliferating and invasive cells as seen in the first trimester trophoblast further confirms its in vivo role in maintaining control of proliferation. On the other hand, their increased expression in tumors associated with an altered developmental peptide profile support the view that altered expression as a cause or consequence of malignant transformation and thereby, the use of developmental peptides as biomarkers, or therapeutics is envisaged. Developmental peptides appear to act through specific receptors that are expressed by abnormal and not normal cells. As such, as seen in the embryo, developmental peptides appear to act locally on the receptor target aimed in eliminating abnormal cells. As such, homeostasis in the body is maintained where normal cells secrete and abnormal cells respond to developmental peptides. One aspect of the present invention provides a method for identifying the developmental peptide receptor and creating a pharmacophore to examine developmental peptide/receptor interaction.

SUMMARY OF THE INVENTION

One aspect of the present invention provides for developmental peptides, peptidomimetics and methods of their use for inhibiting abnormal cell proliferation.

Thus, according to one aspect of the invention, a synthetic developmental peptide is provided, which binds to a developmental peptide receptor and inhibits abnormal cellular proliferation. The developmental peptide is preferably a seven to eleven amino acid peptide. In preferred embodiments, the developmental peptide comprises the sequence N-Gly-Lys-Arg-Ile-Lys-Gly-Thr-OH (SEQ ID No.1). In other embodiments, the developmental peptide comprises the sequence of N-Val-Leu-Gly-Lys-Arg-Ile-Lys-Gly-Thr-OH (SEQ ID No.2), N-Ile-Glu-Val-Leu-Gly-Lys-Arg-Ile-Lys-Gly-Thr-OH (SEQ ID No.3), N-Ile-Asp-Val-Leu-Gly-Lys-Arg-Ile-Lys-Gly-Thr-OH (SEQ ID No.4), N-Ile-Arg-Val-Leu-Gly-Lys-Arg-Ile-Lys-Gly-Thr-OH (SEQ ID No.5), N-Ile-Glu-Val-Thr-Gly-Lys-Arg-Ile-Lys-Gly-Thr-OH (SEQ ID No.6), N-Ile-Asp-Val-Thr-Gly-Lys-Arg-Ile-Lys-Gly-Thr-OH (SEQ ID No.7), or N-Ile-Arg-Val-Thr-Gly-Lys-Arg-Ile-Lys-Gly-Thr-OH (SEQ ID No.8), Gly-Lys-Arg-Ile (SEQ ID No.9), or Lys-Gly-Thr. In further embodiments, the developmental peptide has the sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof.

The present invention also provides for non-peptide or partial peptide mimetic of any of the aforementioned developmental peptides.

In another aspect, the present invention provides for a method of inhibiting abnormal cellular proliferation comprising administering the aforementioned developmental peptides or peptidomimetics in an amount sufficient to inhibit abnormal proliferation. In another embodiment, the cell is disposed within a living organism, preferably a mammal, more preferably a human.

In a further aspect of the invention, a compound that binds to developmental peptide receptors and inhibits abnormal cell proliferation is provided. The compound has the formula $R_1$—$R_2$—$R_3$—$R_4$—$R_5$—$R_6$—$R_7$—OH, wherein $R_1$ is Gly or a mimetic of Gly, $R_2$ is Lys or a mimetic of Lys, $R_3$ is Arg or a mimetic of Arg, $R_4$ is Ile or a mimetic of Ile, $R_5$ is Lys or a mimetic of Lys, $R_6$ is Gly or a mimetic of Gly and $R_7$ is Thr or a mimetic of Thr. In alternative embodiments, the compound may comprise the formula X—$R_1$—$R_2$—$R_3$—$R_4$—$R_5$—$R_6$—$R_7$—OH, wherein X may comprise two to four amino acid residues or mimetics of said residues, $R_1$ is Gly or a mimetic of Gly, $R_2$ is Lys or a mimetic of Lys, $R_3$ is Arg or a mimetic of Arg, $R_4$ is Ile or a mimetic of Ile, $R_5$ is Lys or a mimetic of Lys, $R_6$ is Gly or a mimetic of Gly and $R_7$ is Thr or a mimetic of Thr. For example, X may comprise the sequence Val-Leu, Ile-Glu-Val-Leu, Ile-Asp-Val-Leu, Ile-Arg-Val-Leu, Ile-Glu-Val-Thr, Ile-Asp-Val-Thr, Ile-Arg-Val-Thr, or mimetics thereof.

The present invention also provides for a methodology for isolating developmental peptides from adult and embryonal tissues that have selective antiproliferative effects on damaged cells, including, for example, cancerous cells and virally infected cells, as compared to normal cells. This methodology in one of its non-limiting embodiments allows for isolation and identification of developmental peptides containing a seven amino acid sequence N-Gly-Lys-Arg-Ile-Lys-Gly-Thr-OH (SEQ ID No.1) present in both embryonal and adult mammalian tissue. More preferably, the developmental peptide is of the sequence N-Val-Leu-Gly-Lys-Arg-Ile-Lys-Gly-Thr-OH (SEQ ID No.2) that is present in both embryonal and adult mammalian liver. The developmental peptide may be isolated using chromatographic techniques or other isolation techniques known in the art.

In another embodiment, a method for identifying and analyzing developmental peptides and developmental peptide-like sequences within a protein database is provided. Preferably, the analysis is performed on Val-Leu-Gly-Lys-Arg-Ile-Lys-Gly-Thr (SEQ ID No.2) versus the human protein database.

A further embodiment of the present invention relates to the characterization and sequencing of a peptide that has significant antiproliferative effects on mammalian cancer cells. Preferably the developmental peptide has a sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof.

For example, the present invention relates to demonstrating the developmental peptide antiproliferative effect against various cancer cells including but not limited to breast and androgen receptor negative prostate cancer cells. In a further non-limiting embodiment, the present invention relates to demonstrating developmental peptide antiproliferative effect against various virally infected cells. While not wanting to be limited by theory, the antiproliferative effect may be exerted by blocking protein synthesis and creating mitochondrial collapse. The antiproliferative effect could also be exerted against leukemia and cancerous cells of the lung, liver, kidney, ovary, uterus, colon and the like.

Further, methods of inhibiting cancer cell proliferation comprising administering an effective amount of developmental peptides or peptidomimetic thereof to a subject in need of such treatment. As such, the proteins, peptides and peptidomimetics of the invention may be useful for the treatment of cancer and other proliferative disorders. In a further embodiment, a method of potentiating chemotherapeutic agents by administering a developmental peptide or mimetic thereof is provided. Methods of inhibiting viral replication and proliferation comprising administering an effective amount of developmental peptides or a peptidomimetic thereof to a subject in need of such treatment. In addition, administration of developmental peptides before and during pregnancy may help reduce/eliminate teratogenicity/toxicity of different compounds or exposures.

In a further embodiment of the present invention, a method of generating synthetic developmental peptides that exhibit the same or substantially similar activity of the native peptide is provided. Preferably, the synthetic developmental peptides are of 70% homology or greater to the native peptide. In preferred embodiments, the developmental peptide developmental peptide has the sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof.

In another embodiment of the present invention, a method of identifying specific receptor sites present on various tissues and cells that bind to developmental peptides with the effects being transduced by binding to the developmental peptide receptor sites is provided.

In a further embodiment, a method of identifying and cloning the genes that are responsible for developmental peptide expression, including N-Val-Leu-Gly-Lys-Arg-Ile-Lys-Gly-Thr-OH (SEQ ID No.2) or related peptides.

The present invention also provides for pharmaceutical compositions comprising said developmental peptides and peptidomimetics thereof isolated by the described methodology. Administration of the developmental peptides or mimetic may be carried out using oral, enteral, parental or topical administration, including, for example, intravenous, oral, transdermal or any other mode of administration with appropriate vehicle. The developmental peptides may be used alone or in combination with other agents like chemotherapy, or immune based therapy.

Another embodiment of this invention is the isolation and cloning of developmental peptide receptors or related proteins that transduce the peptide or in general developmental peptide effects. This method also provides for identifying the intracellular mechanisms including but not limited to the transcription factors that lead to the changes noted in protein synthesis and mitochondrial collapse. Also the method may allow for the identification of the developmental peptide secretory products that are modified following exposure to developmental peptides. It also provides the method for identifying the genes' expression that are modified secondary to exposure to the peptide.

In an additional embodiment, the present invention relates to method of generating an antibody against developmental peptides and testing the antibody using immunohistochemistry in tissue arrays of humans and mouse. Assays could be used to monitor tumor presence, viral infection and response to therapy in both tissues and isolated cells. The assays provide a method for determining embryonal health during pregnancy and monitoring pregnancy well being. Specifically, the method provides determination of endogenous developmental peptide expression and its relation to cell proliferation, invasion and differentiation under normal and pathological conditions. The method is applicable for all developmental peptides and may be used to provide a diagnostic method that reflects the body homeostasis in all mammals.

In an additional embodiment, the present invention relates to a method for biomarker discovery by identifying developmental peptides in biological fluids such as serum, urine, saliva, ascites. This method entails generating affinity columns using anti-developmental peptide antibodies and examining collected samples by mass spectrometry, gel electrophoresis or by chromatographic methods. Use of deuterium labeled developmental peptides as internal standards may allow for evaluating precise recovery of each sample.

In another embodiment, the present invention relates to a method using the developmental peptide antibody for isolating and characterizing developmental peptides that share a sequence homology with developmental peptide has the sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof; or the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof; more preferably N-Val-Leu-Gly-Lys-Arg-Ile-Lys-Gly-Thr-OH (SEQ ID No.2) by any method including, but not limited to, affinity chromatography, Western blot, 2 D gel electrophoresis, and mass spectrometry. In addition, identification of the pro-protein that encompasses the sequence will allow identification of the genes responsible for the encoding peptide and identify steps involved in the protein synthesis and processing that appears to be altered in cancer. In one non-limiting embodiment, the current method will allow for identification of protein to protein interactions and identification of functions of several human endogenous retroviral particles (HERVs). As such, the current method structure provides a method to determine the functional relationship between controllers of proliferation and fundamental cellular structures that are critical for cell survival such as gamma actin and the like. Also these methods allow for identification of the human gene and cloning of the gene that is responsible for developmental peptides and related proteins, as well those that interact with developmental peptides.

The present invention provides a screening method using mammalian embryos and labeled developmental peptides to determine whether compounds are teratogenic, toxic, mutagenic, carcinogenic or infectious. As such it could provide a cost effective and sensitive method to eliminate potentially noxious compounds from the environment. As such the method could be used also for biodefense purposes to examine developmental peptides binding to other cells such as in saliva to determine whether exposure to a potentially toxic or infectious agent has occurred

BRIEF DESCRIPTION OF THE FIGURES

The file of this patent contains at least one photograph or drawing executed in color. Copies of this patent with color drawing(s) or photograph(s) will be provided by the Patent and Trademark Office upon request and payment of necessary fee.

For a fuller understanding of the nature and advantages of the present invention, reference should be had to the following detailed description taken in connection with the accompanying drawings.

FIG. 5 illustrates the sequence of the novel 970 Daltons peptides (i.e., SEQ ID NOs. 3, 4, 5, 6, 7, and 8, respectively) and the shared homology with a portion of the retrovirus enzyme.

DETAILED DESCRIPTION

Figure 1:
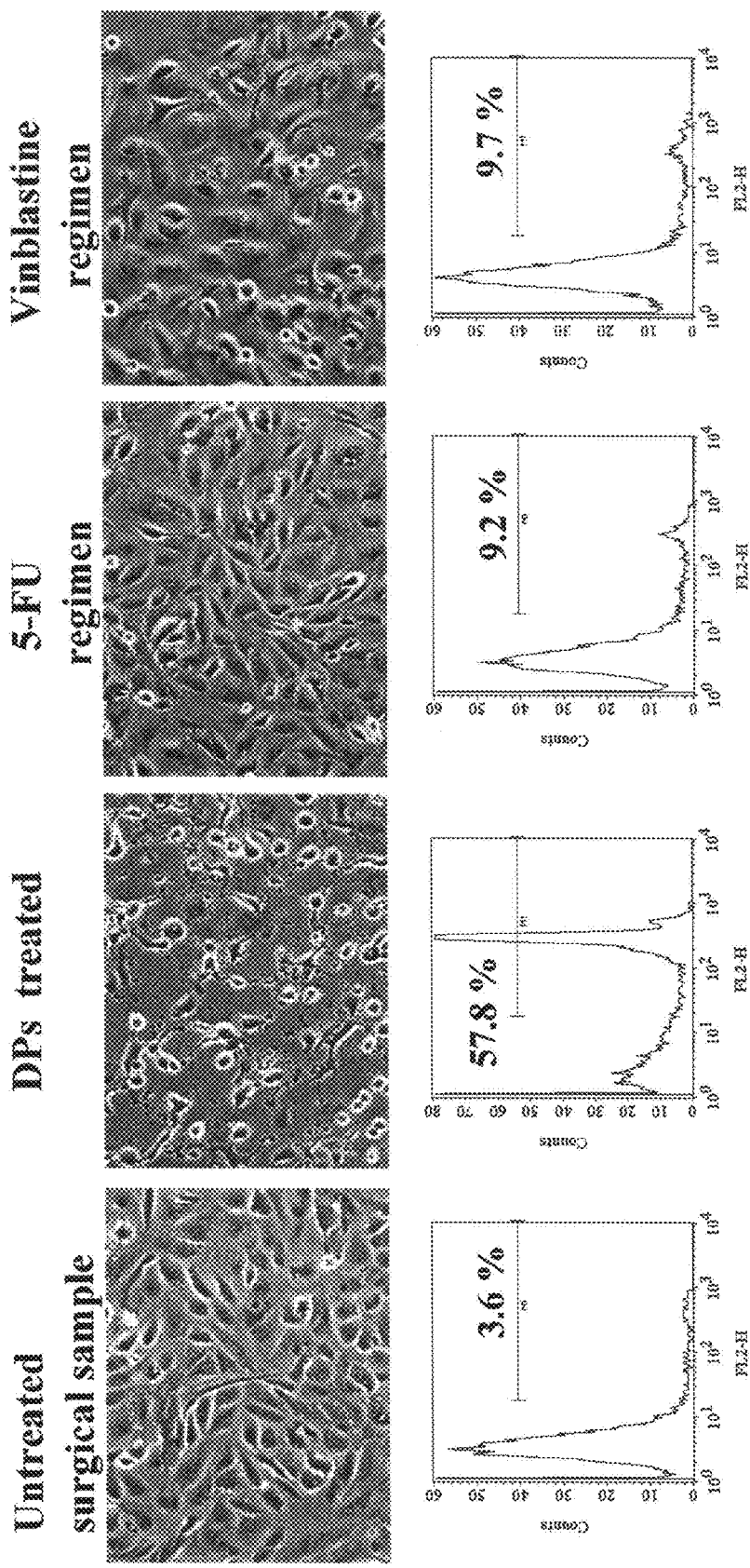
FIG. 1 shows that cells isolated from renal cancer specimen were completely inhibited by addition of highly purified adult porcine liver derived developmental peptides <3000 kDa. In contrast, two type of chemotherapy even in high doses had no effect. Developmental peptides effect cause collapse of the cells and loss of cell to cell contact. A 99% dose dependent inhibition of cells derived from a metastatic stage IV tubal epithelial carcinoma surgical sample was also demonstrated (data not shown).

Before the present compositions and methods are described, it is to be understood that this invention is not limited to the particular molecules, compositions, methodologies or protocols described, as these may vary. It is also to be understood that the terminology used in the description is for the purpose of describing the particular developmental peptide versions or embodiments only, and is not intended to limit the scope of the present invention.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

In one embodiment, the developmental peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7 membered alkyl, amide, amide lower alkyl, amide di (lower alkyl), lower alkoxy, hydroxy, carboxy and the lower ester derivatives thereof, and with 4-, 5-, 6-, to 7 membered heterocyclics. For example, proline analogs can be made in which the ring size of the proline residue is changed from 5 members to 4, 6, or 7 members. Cyclic groups can be saturated or unsaturated, and if unsaturated, can be aromatic or nonaromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, Ann. Rep. Med. Chem. 24, 243-252, 1989). Certain peptidomimetic compounds are based upon the amino acid sequence of the peptides of the invention. Often, peptidomimetic compounds are synthetic compounds having a three-dimensional structure (i.e. a "peptide motif) based upon the three-dimensional structure of a selected peptide. The peptide motif provides the peptidomimetic compound with the desired biological activity, i.e., binding to IAP, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, Curr. Op. Chem. Biol. 2, 441-452, 1998; Hruby et al., Curr. Op. Chem. Biol. 1, 114-119, 1997; Hruby & Balse, Curr. Med. Chem. 9, 945-970, 2000). One class of peptidomimetics a backbone that is partially or completely non-peptide, but mimics the peptide backbone atom-for atom and comprises side groups that likewise mimic the functionality of the side groups of the native amino acid residues. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

Thus, according to one aspect of the invention, a synthetic developmental peptide is provided, which binds to a developmental peptide receptor and inhibits abnormal cellular proliferation. The developmental peptide is preferably a seven to eleven amino acid peptide. In preferred embodiments, the developmental peptide comprises the sequence N-Gly-Lys-Arg-Ile-Lys-Gly-Thr-OH (SEQ ID No.1). Abnormal cellular proliferation may include, for example, cancer or viral infection.

Inhibition of abnormal cellular proliferation by developmental peptides involves control of proliferation by elimination of damaged cells without interfering with normal cell proliferation and without being toxic. To eliminate damaged cells, developmental peptides may use several pathways and processes which involve a cascade to include known pathways, simultaneously or sequentially, until the damaged cell is unable to replicate or transmit its damage, culminating in the damaged cell's death. Damaged cells include cancer cells or those cells infected with a virus.

In other embodiments, the developmental peptide comprises the sequence of N-Val-Leu-Gly-Lys-Arg-Ile-Lys-Gly-Thr-OH (SEQ ID No.2), N-Ile-Glu-Val-Leu-Gly-Lys-Arg-Ile-Lys-Gly-Thr-OH (SEQ ID No.3), N-Ile-Asp-Val-Leu-Gly-Lys-Arg-Ile-Lys-Gly-Thr-OH (SEQ ID No.4), N-Ile-Arg-Val-Leu-Gly-Lys-Arg-Ile-Lys-Gly-Thr-OH (SEQ ID No.5), N-Ile-Glu-Val-Thr-Gly-Lys-Arg-Ile-Lys-Gly-Thr-OH (SEQ ID No.6), N-Ile-Asp-Val-Thr-Gly-Lys-Arg-Ile-Lys-Gly-Thr-OH (SEQ ID No.7), or N-Ile-Arg-Val-Thr-Gly-Lys-Arg-Ile-Lys-Gly-Thr-OH (SEQ ID No.8). In further embodiments, the developmental peptide contains the sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof.

The present invention also provides for non-peptide or partial peptide mimetic of any of the aforementioned developmental peptides.

In another embodiment of the present invention, identification and sequence analysis of developmental peptides or developmental peptide-like molecules is performed on a known protein database. Preferably, a blast search is performed Val-Leu-Gly-Lys-Arg-Ile-Lys-Gly-Thr (SEQ ID No.2) versus the human protein database.

A further embodiment of the present invention relates to the characterization and sequencing of a peptide that has significant antiproliferative effects on damaged mammalian cells, for example cancer cells and virally infected cells. Preferably the developmental peptide contains the sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. For example, the present invention relates to demonstrating the developmental peptide antiproliferative effect against various cancer cells including but not limited to breast and androgen receptor negative prostate cancer cells. The antiproliferative effect could also be exerted against leukemia and cancerous cells of the lung, liver, kidney, ovary, uterus, colon and the like. The present invention also relates to demonstrating the developmental peptide antiproliferative effect against virally infected cells, including, but not limited to cells infected with retroviruses such as HIV. While not wanting to be limited by theory, the antiproliferative effect may be exerted by blocking protein synthesis, blocking survival factors, promoting death signals and creating mitochondrial collapse. Further the effect may be achieved by blocking oncogenic pathways, including but not limited to ras-raf, src kinase, and IP3 kinase, activating phosphatases, and blocking angiogenesis and blocking NFkB activity.

In a further aspect of the invention, a compound that binds to developmental peptide receptors and inhibits abnormal cell proliferation is provided. The compound has the formula $R_1$—$R_2$—$R_3$—$R_4$—$R_5$—$R_6$—$R_7$—OH, wherein $R_1$ is Gly or a mimetic of Gly, $R_2$ is Lys or a mimetic of Lys, $R_3$ is Arg or a mimetic of Arg, $R_4$ is Ile or a mimetic of Ile, $R_5$ is Lys or a mimetic of Lys, $R_6$ is Gly or a mimetic of Gly and $R_7$ is Thr or a mimetic of Thr. In alternative embodiments, the compound may comprise the formula X—$R_1$—$R_2$—$R_3$—$R_4$—$R_5$—$R_6$—$R_7$—OH, wherein X may comprise two to four amino acid residues or mimetics of said residues, $R_1$ is Gly or a mimetic of Gly, $R_2$ is Lys or a mimetic of Lys, $R_3$ is Arg or a mimetic of Arg, $R_4$ is Ile or a mimetic of Ile, $R_5$ is Lys or a mimetic of Lys, $R_6$ is Gly or a mimetic of Gly and $R_7$ is Thr or a mimetic of Thr. For example, X may comprise the sequence Val-Leu, Ile-Glu-Val-Leu, Ile-Asp-Val-Leu, Ile-Arg-Val-Leu, Ile-Glu-Val-Thr, Ile-Asp-Val-Thr, Ile-Arg-Val-Thr, or mimetics thereof.

The present invention also provides for a methodology for isolating developmental peptides from adult and embryonal tissues that have selective antiproliferative effects on cancerous tissue and cancerous cells or virally infected cells as compared to normal cells. This methodology in one of its non-limiting embodiments allows for isolation and identification of developmental peptides containing a four amino acid sequence of $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof, or a seven amino acid sequence N-Gly-Lys-Arg-Ile-Lys-Gly-Thr-OH (SEQ ID No.1) present in both embryonal and adult mammalian tissue. More preferably, the developmental peptide is of the sequence N-Val-Leu-Gly-Lys-Arg-Ile-Lys-Gly-Thr-OH (SEQ ID No.2) that is present in both embryonal and adult mammalian liver. The developmental peptide may be isolated using chromatographic techniques or other isolation techniques known in the art.

The present invention also provides for pharmaceutical compositions comprising said developmental peptides and peptidomimetics thereof isolated by the described methodology. Preferably the developmental peptide comprises the sequence N-Gly-Lys-Arg-Ile-Lys-Gly-Thr-OH (SEQ ID No.1), N-Val-Leu-Gly-Lys-Arg-Ile-Lys-Gly-Thr-OH (SEQ ID No.2), N-Ile-Glu-Val-Leu-Gly-Lys-Arg-Ile-Lys-Gly-Thr-OH (SEQ ID No.3), N-Ile-Asp-Val-Leu-Gly-Lys-Arg-Ile-Lys-Gly-Thr-OH (SEQ ID No.4), N-Ile-Arg-Val-Leu-Gly-Lys-Arg-Ile-Lys-Gly-Thr-OH (SEQ ID No.5), N-Ile-Glu-Val-Thr-Gly-Lys-Arg-Ile-Lys-Gly-Thr-OH (SEQ ID No.6), N-Ile-Asp-Val-Thr-Gly-Lys-Arg-Ile-Lys-Gly-Thr-OH (SEQ ID No.7), or N-Ile-Arg-Val-Thr-Gly-Lys-Arg-Ile-Lys-Gly- Thr-OH (SEQ ID No.8). In further embodiments, the developmental peptides contain the sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof.

The developmental peptides and mimetics may be administered in an effective amount to a subject in need of such treatment. As such, the proteins and peptides described herein may be useful for the treatment of cancer and other proliferative disorders, including viral infections. Administration of the developmental peptides or peptidomimetic, in the form of a therapeutic agent, may be carried out using oral, enteral, parenteral or topical administration, including, for example, intravenous, oral, transdermal or any other mode of administration with appropriate vehicle. The developmental peptide or mimetic thereof may used alone or in combination with other agents.

Pharmaceutical compositions can be used in the preparation of individual dosage forms. Consequently, pharmaceutical compositions and dosage forms of the invention comprise the active ingredients disclosed herein (i.e., developmental peptides, or mimetics thereof). Pharmaceutical compositions and dosage forms of the invention can further comprise one or more excipients.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an amount of from about 1 mg to about 2000 mg, more preferably from about 50 mg to about 1000 mg, even more preferably from about 100 mg to about 750 mg, and more preferably from about 200 mg to about 500 mg.

In another aspect, the present invention provides for a method of inhibiting abnormal cellular proliferation comprising administering the aforementioned developmental peptides or peptidomimetics in an amount sufficient to inhibit abnormal proliferation. In another embodiment, the cell is disposed within a living organism, preferably a mammal, more preferably a human.

Further, methods of inhibiting cancer cell proliferation comprising administering an effective amount of developmental peptides or peptidomimetics of said developmental peptides to a subject in need of such treatment. Additionally, methods of inhibiting viral replication and proliferation comprising administering an effective amount of developmental peptides or peptidomimetics of said developmental peptides to a subject in need of such treatment. As such, the proteins, peptides and peptidomimetics of the invention may be useful for the treatment of cancer, viral infections and other proliferative disorders.

Developmental peptides could be used alone or in combination with chemotherapeutic agents or immunotherapies. Developmental peptides may be administered orally, parenterally, enterally, nasally, transmucosally or by inhalation and the like. Developmental peptides may exert their antiproliferative effects against cancer, including, but not limited to cancers of the prostate, kidney, fallopian tube, or breast. Such cancer can be early stage or advanced form, including metastatic cancer. The developmental peptides can be given also for the treatment preneoplastic lesions or as prevention for the development of malignancy. Therefore one of the embodiments of the invention is the use of developmental peptides to combine with chemotherapy to lower the toxicity of a chemotherapeutic agent by allowing for a reduction in the doses of the currently used chemotherapeutic agents.

The developmental peptides, or mimetics thereof, are preferably administered in effective amounts. An effective amount is that amount of a preparation that alone, or together with further doses, produces the desired response. This may involve only slowing the progression of the disease temporarily, although preferably, it involves halting the progression of the disease permanently or delaying the onset of or preventing the disease or condition from occurring. This can be monitored by routine methods. Generally, doses of active compounds would be from about 0.01 mg/kg per day to 1000 mg/kg per day. It is expected that doses ranging from 50-500 mg/kg will be suitable, preferably intravenously, intramuscularly, or intradermally, and in one or several administrations per day. The administration of the developmental peptides, or mimetics thereof, can occur simultaneous with, subsequent to, or prior to chemotherapy or radiation so long as the chemotherapeutic agent or radiation sensitizes the system to the developmental peptides, or mimetics thereof.

In general, routine experimentation in clinical trials will determine specific ranges for optimal therapeutic effect for each therapeutic agent and each administrative protocol, and administration to specific patients will be adjusted to within effective and safe ranges depending on the patient condition and responsiveness to initial administrations. However, the ultimate administration protocol will be regulated according to the judgment of the attending clinician considering such factors as age, condition and size of the patient, the developmental peptides, or mimetics thereof, potencies, the duration of the treatment and the severity of the disease being treated. For example, a dosage regimen of the developmental peptides, or mimetics thereof, can be oral administration of from 1 mg to 2000 mg/day, preferably 1 to 1000 mg/day, more preferably 50 to 600 mg/day, in two to four (preferably two) divided doses, to reduce tumor growth. Intermittent therapy (e.g., one week out of three weeks or three out of four weeks) may also be used.

In the event that a response in a subject is insufficient at the initial doses applied, higher doses (or effectively higher doses by a different, more localized delivery route) may be employed to the extent that the patient tolerance permits. Multiple doses per day are contemplated to achieve appropriate systemic levels of compounds. Generally, a maximum dose is used, that is, the highest safe dose according to sound medical judgment. Those of ordinary skill in the art will understand, however, that a patient may insist upon a lower dose or tolerable dose for medical reasons, psychological reasons or for virtually any other reason.

In another non-limiting embodiment, the present invention relates to demonstrating the developmental peptide antiproliferative effect against various cancer cells, including, but not limited to, breast, and androgen receptor negative prostate cancer cells. The antiproliferative effect is dose dependent and the effective concentration shows no notable effect on normal cells or embryos. While not wanting to be limited by theory, the antiproliferative effect may be exerted by blocking protein synthesis and creating mitochondrial collapse. The antiproliferative effect could also be exerted against leukemia cells, or abnormal cells of the lung, liver, kidney, ovary, uterus, colon and the like.

In a further embodiment, a method of potentiating chemotherapeutic agents by administering a developmental peptide or peptidomimetic thereof as described herein. For example, in the method, a chemotherapeutic agent that alone was not effective or fully effective, will become effective when developmental peptides are added to the therapy resulting in an antiproliferative effect. Such a method is useful when the agents alone are not effective, or when treatment agents are effective but are highly toxic, enabling their dose to be lowered and therefore toxicity could be limited or eliminated altogether.

In a further embodiment of the present invention, a method of generating synthetic developmental peptides that exhibit the same or substantially similar activity of the native peptide is provided. Preferably, the synthetic developmental peptides are of 70% homology or greater to the native peptide. In preferred embodiments, the developmental peptide has the following sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof.

In a further embodiment, a method of identifying and cloning the genes that are responsible for developmental peptide expression. In a preferred embodiment, the gene identified and cloned is responsible for the peptide of SEQ ID NO: 2.

In another embodiment of the present invention, a method of identifying specific receptor sites present on various tissues and cells that bind to developmental peptides and are transduced by binding to the developmental peptides receptor sites is provided.

Another embodiment of this invention is the isolation and cloning of developmental peptide receptors or related proteins that transduce the peptide or in general developmental peptide effects. This method also provides for identifying the intracellular mechanisms including but not limited to the transcription factors that lead to the changes noted in protein synthesis and mitochondrial collapse. Also the method may allow for the identification of the developmental peptide secretory products that are modified following exposure to developmental peptides, such as, but not limited to, cytokines and growth factors. It also provides the method for identifying the genes' expression that are modified secondary to exposure to the peptide. This embodiment also includes the use of labeled developmental peptides for diagnostic purposes both in vitro and when administered in vivo.

The present invention provides a method for isolating and characterizing a novel developmental peptide antiproliferative peptide of SEQ ID NO: 2 in one non limiting embodiment. Accordingly, the present invention provides for therapeutic compositions comprising the developmental peptide or a protein that contains the peptide prepared by chemical synthesis and for selectively inhibiting the proliferation of cancer cells. In particular, in non-limiting embodiments, the present invention provides for antiproliferative compositions where the protein may have anti-proliferative effects, for example but not limited to, in an assay of MCF-7 breast cancer cells and PC3 prostate cancer cells, where proliferation is inhibited by at least 30% and preferably by at least 75%, or by adding developmental peptides to a chemotherapeutic agent to enhance the efficacy of the anti-cancer treatment regimen by rendering the chemotherapeutic agent effective against cancer in models and patients where the chemotherapeutic agent failed to do so alone. The composition may further comprise a suitable pharmaceutical carrier and optionally one or more additional bioactive agent.

The agents of the invention could be used as antiproliferative agents to protect from a pre-malignant to malignant transformation or decrease proliferation of malignant cells. The antiproliferative effects may be produced in vitro or in vivo. In particular, but not limiting, developmental peptides may be used to prevent or treat cancers involving breast, prostate, kidney, bone, liver, melanoma, colon, skin, testicle, and ovary among others. The compositions of the invention may thus be used to prevent or to inhibit the growth or spread of malignant cells in a subject in need of such treatment.

In one preferred current embodiment, the peptide is N-Val-Leu-Gly-Lys-Arg-Ile-Lys-Gly-Thr-OH (SEQ ID NO: 2) or above 70% sequence homology. This sequence shares partial homology with the pol protein (a portion of the endogenous reverse transcriptase) of simian type retrovirus. Such peptides could be modified by conjugation to another compound where the compound is selected from the group including, but not limited to, other proteins (e.g. immunoglobulin molecules or fragments of), lipids and carbohydrate residues, pharmaceutical agents, polyethylene glycol, etc., or may incorporated into a larger peptide or protein (e.g., a fusion protein).

The present invention provides for isolated nucleic acids encoding the peptides of the invention. Such peptides may be comprised in a suitable vector for cloning and or expression.

The present invention also provides for developmental peptides as set forth by producing combinatorial mixtures of the possible peptides. The peptides may be prepared from natural sources, chemically synthesized or produced recombinant DNA methods. The present invention also provides for the introduction, into a subject of a nucleic acid encoding one or more of the foregoing peptides are expressed. The subject may be a microorganism, such as bacterium, yeast, a eukaryotic cell, such as mammalian, insect, or plant cell, may be multicellular organism such as a mammal or bird.

The antiproliferative developmental peptides of the invention may be used in methods of inhibiting cell proliferation and particularly inhibiting malignant cell proliferation. They may be administered in an effective dose and in suitable pharmaceutical carrier to a subject in need of such treatment. Administration methods include but are not limited to topical, intravenous, intraperitoneal, intrapulmonary, intrathecal, subcutaneous as well as a local injection into a tissue or tumor. Proliferative conditions that may benefit from the administration of the developmental peptides of the invention include, but are not limited to, cancer, including but not limited to breast, prostate, kidney, colon, bladder, melanoma, leukemia, as well as pre-malignant lesions of different organs and hyperproliferative conditions such as rheumatoid arthritis and keloid formation.

Additional embodiment is using labeled developmental peptides as a screening tool to examine effect of various mutagens/toxic agents/carcinogens and infectious agents on normal and developmental tissues in a preclinical setting. This could be useful for the examination of adverse environments, pollutants and agents for example (not to be limiting in any manner) in the development for clinical use, wherein positive results may lead to removal of the offending agents or avoidance of exposure to them, including biodefense. While in drug discovery it could be a rapid tool to modify compounds to limit their toxicity towards a more acceptable profile.

In an additional embodiment, the present invention relates to method of generating an antibody against developmental peptides. The antibody may be a monoclonal or polyclonal antibody, and further the antibody may be IgA, IgG, IgM, IgD, IgE, and more preferably IgY. In a further embodiment, the antibody may be tested using immunohistochemistry in tissue arrays of humans and mouse. Assays could be used to monitor tumor presence and response to therapy. The assays provide a method for determining embryonal health during pregnancy and monitoring pregnancy well being using various body fluids and tissues. The assays could be used to identify developmental peptide related biomarkers in various non pregnant biological fluids as well by using ELISA, affinity chromatography or other non-limiting detection method.

Identification of altered proteins/peptides related to developmental peptides due to disease would aid in the identification of other biomarkers. Using deuterium labeled developmental peptides as an internal standard, for example in the valine and/or leucine amino acid, would help to monitor recovery and sensitivity of the assay. The method is applicable for all developmental peptides and may be used to provide a diagnostic method, as well biomarkers for disease, that reflects the body homeostasis in all mammals. Preferably, the antibody is generated against SEQ ID No.2.

In another embodiment, the present invention relates to a method using the developmental peptides antibody for isolating and characterizing developmental peptides that share a sequence homology with developmental peptides, preferably of the amino acid sequence $Xaa_m$-Gly-Lys-Arg-Ile-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof. In further embodiments, the developmental peptide has the sequence $Xaa_m$-Lys-Gly-Thr-$Xaa_n$, wherein $Xaa_m$ and $Xaa_n$ each represent an amino acid and wherein m independently has a value from 0 to 20, preferably less than 10, and wherein n independently has a value from 0 to 20, preferably less than 10, or mimetics thereof, more preferred N-Val-Leu-Gly-Lys-Arg-Ile-Lys-Gly-Thr-OH (SEQ ID No.2) by any method including, but not limited to, affinity chromatography, Western blot, 2 D gel electrophoresis, and mass spectrometry. In addition, identification of the pro-protein that encompasses the sequence will allow identification of the genes responsible for the peptide encoding and identify steps involved in the protein synthesis and processing that appears to be altered in cancer. In one non-limiting embodiment, the current method will allow for identification of protein to protein interaction and identification of the function of several HERVs. The method also allows examination of the relationship between elements involved in cell proliferation, differentiation and invasivity, such as use of cell proliferation markers Ki67 and HSP 27 for example, in normal and pathologic samples. As such, the current method structure provides a method to determine the functional relationship between controllers of proliferation and fundamental cellular structures that are critical for cell survival such as gamma actin and the like. Also these methods allow for identification of the human gene and cloning of the gene that is responsible for developmental peptides and related proteins, as well those that interact with developmental peptides.

In another embodiment, the present invention relates to method of generating a chicken antibody (IgY) against the developmental peptides, preferably SEQ ID No.2, and testing the antibody using immunohistochemistry in tissue arrays of humans and mouse. This embodiment is based, at least in part on the finding that the expression of the peptide/protein that contains the peptide is present mostly in epithelial cells as well as pancreas where the highest expression was noted. The expression of developmental peptides using IgY was hundreds of fold higher in a 60 tumor panel epithelium than in normal tissues. For example, antibody production could be made in rabbits, goats and mice, poly and monoclonal, used as diagnostic methods in vitro as well as in vivo for determining developmental peptide levels in biological fluids (such as blood, urine, saliva, embryo culture media and the like), tissues and cells using ELISA, EIA or lateral flow assay as well as the antibody can be injected to image tumors in the body as non limiting examples.

The assays could be used to monitor tumor presence, and response to therapy. The assays provide a method for determining embryonal health during pregnancy and monitoring pregnancy well being The method is applicable for all developmental peptides and related proteins and may be used to provide a diagnostic method that reflects the body's homeostasis in all mammals.

In another embodiment, the present invention relates to a method using the IgY antibody or IgG monoclonal antibody for isolating and characterizing developmental peptides that share a sequence homology with antiproliferative developmental peptides by any method including, but not limited to, affinity chromatography, Western blot, 2 D gel electrophoresis, and mass spectrometry and the like. This is based on the demonstration of differential expression between a normal and a hepatocarcinoma sample. Since the human placenta, analyzed using a Western blot, has a similar protein expression profile as adult tissue the methodology described using, in a non limiting manner, affinity chromatography allows for isolation of additional peptides that may have potency, efficacy and selectivity of action that is even greater than SEQ ID NO: 2. In addition, identification of the pro-protein that encompasses the peptide will allow for the identification of genes encoding the peptide and also allow the identification of steps involved in the protein synthesis and processing that appears to be altered in cancer.

Using the IgY dependent affinity chromatography coupled with mass spectrometry, sequencing suggested that the larger developmental peptides may be attached to cytoskeleton proteins and RNA polymerase and human endogenous retrovirus proteins within the cell. Therefore current methodology, in a non limiting embodiment, will allow for identification of protein to protein interaction(s) and the identification of the function of several HERV. As such, the current method structure provides a method to determine the functional relationship between controllers of proliferation and fundamental cellular structures that are critical for cell survival, such as gamma actin and the like. Also these methods allow for identification of the human gene(s) and cloning of the gene(s) responsible for developmental peptides and related proteins, as well those that interact with developmental peptides.

These non limiting examples show that other developmental peptides may also be present both in fetal and adult tissues which sequences could serve as diagnostics for documenting abnormal cell proliferation and could be the basis for generation of specific antibodies IgY, IgG, and monoclonal as non limiting examples. Further evidence is provided by first trimester placental explants where co-localization of proliferation and invasivity markers (Ki67 and HSP27) was found with developmental peptides. In this context developmental peptides could limit neoplastic like cytotrophoblast and extravillous trophoblast proliferation and invasion.

Developmental peptide antibodies could be used for biomarker discovery and validation in biological fluids including serum, urine, saliva, ascites this by using developmental peptides detection through, for example, developmental peptides ELISA, or affinity chromatography. To that end a developmental peptide (SEQ ID NO: 2) was generated using deuterium labeled Leu (mass+10) as one peptide and Val (mass+8) and Leu (mass 10) for a total 18 for the other. This is used to monitor peptide recovery following affinity chromatography and mass spectrometry for quantitative assessment.

Also the analysis of tumor samples could be carried out by various chromatographical methods using the antibody as well as 2D gel electrophoresis, mass spectrometry, HPLC, etc., in a non limiting manner. In addition presence of the antibodies could be used for the development of quantitative assays for measuring the concentration of developmental peptides and related proteins in biological samples and fluids, by using ELISA, lateral flow EIA, etc., as non limiting examples.

The developmental peptides and peptidomimetics thereof in the present invention may be coupled to labels, including but not limited to FITC, biotin, rhodamine, radioactive labels, fluorescent nanocrystals, and other labels known to those skilled in the art. The labeled developmental peptides could be used by introducing a labeled developmental peptide molecule by injection into the body, labeling may be with fluorescence, for such as but not limited to, rhodamin, biotin, etc. The injected molecule could be used to determine the localization of tumors using radiographic and scanning methods to better diagnose disease and direct therapy.

The labeled developmental peptides and peptidomimetics thereof that may also be used to identify specific receptor sites present on various tissues and cells where the developmental peptide specifically binds as well as the intracellular effects that are transduced by binding to these receptors within the cell. The labeled developmental peptides can be used also to document changes in expression of developmental peptides in pathological conditions due to disease or due to exposure to carcinogens/toxins and infectious agents.

EXAMPLE 1

Isolation of Developmental Peptides and Preparation of Synthetic Developmental Peptides Isolation of the 9AA peptide from the adult mammalian liver. Fresh adult rabbit liver tissues were collected and homogenized on ice with $H_2O$. The samples were centrifuged at 15,000 g and the sample was filtered using Amicon filters 3000-10000 Da, <3000-500, and <500. Fractions collected were tested for activity using the MCF-7 cells. The highest antiproliferative activity was noted at the 3-10 kDa region, the antiproliferative activity of developmental peptides was principally noted in the early fractions with about 99% inhibition of breast cancer cells (MCF-7). Separation by reverse phase HPLC yielded a 90% inhibition of cancer cells.

In a similar manner adult frozen porcine liver was collected and homogenized with $H_2O$ at 4° C. The suspension was centrifuged at 15,000 g and the pellet discarded. The suspension was filtered and the fraction <3000 Da was collected and run using reversed phase HPLC C18 column with a 0-95% acetonitrile gradient. Separation of the active fraction revealed several fractions, in particular at approximately 500-3000 Da regions, that displayed anti-proliferative activity. Antiproliferative activity was tested by collecting the fractions, drying and suspending the sample in media and adding to MCF7 cells for 48 hours. Incorporation of 3H thymidine into cellular DNA of MCF-7 breast cancer cells was used to determine the anti-proliferative activity. The peak fraction that was observed to provide the most anti-proliferative activity was sequenced, yielding a 9 amino acid (AA) peptide of SEQ ID NO: 2.

Almost total inhibition of the cancer cell proliferation was observed with the earlier fractions (fractions in the range of between the $10^{th}$-$16^{th}$ fractions collected). The early bioactive fractions were further separated by a similar reversed phase HPLC, collected, dried down and resuspended in culture media and tested on MCF7 cells. The fraction that yielded the greatest inhibition was submitted for sequencing using the Edman degradation method. The sequence derived was nine amino acid peptide of the sequence N-Val-Leu-Gly-Lys-Arg-Ile-Lys-Gly-Thr-OH (SEQ ID NO: 2).

In order to confirm that the peptide generated has a role in embryo development an embryonal extract was prepared by solubilizing (homogenizing and/or forming a cell lysate) a mammalian porcine embryo liver. While in this example the porcine embryo liver was used, other embryo samples may also be used. For example, the whole embryo may be used to prepare the embryo extract, including but not limited to embryo's derived from a human, pig, cow, horse, sheep or goat; or a portion of an embryo may be used such as the liver, placenta, brain, pancreas. The frozen embryo liver tissue was placed in liquid nitrogen and was grounded to fine powder and then transferred to a 50 ml Falcon tube and 23 ml of C7 solubilizing solution was added. The solution was sonicated with a high power ultrasonic probe for 6×15 seconds (intensity 60%) on ice. The sample was spun down at 21,000 g for 45 minutes in room temperature. The supernatant was removed and the pellet was frozen. To 20 ml of the supernatant 500 ul of the reducing agent was added and 200 ul of the alkylation agent. The solution was let stand for 90 minutes at room temperature. The alkylation reagent was quenched by adding 200 ul Quenching agent. Acetonitrile (ACN) was added to precipitate proteins at 1:5 final volume, such as 20 ml of sample and 80 ml CAN. Samples are spun at 3000 g for 5 minutes, room temperature. The pellet was dried at room temperate for 10 minutes. The pellet was resuspended in Chaps chamber solution. Pellet is allowed to slowly dissolve and protein concentration was determined by Lowry assay. 1 ml of solution was run overnight on MCE 16 hours at 1500 V Maximum. The cathode buffer fraction was removed for CAN precipitation and MALDI analysis. A number of peptides 970-1230 daltons were identified. The 970 dalton developmental peptide was analyzed in detail, which was sequenced by using the Laser mass spec technique. The sequence identified was N-Val-Leu-Gly-Lys-Arg-Ile-Lys-Gly-Thr-OH (SEQ ID NO: 2) the same as that of the adult liver.

Synthetic peptide preparation. The derived 970 dalton developmental peptide sequence was used to generate synthetic peptide N-Val-Leu-Gly-Lys-Arg-Ile-Lys-Gly-Thr-OH (SEQ ID No.2) using solid-phase peptide synthesis (SPPS), carried out on an Applied Biosystems Model 4331A Peptide Synthesizer employing Fmoc chemistry in which the α-amino nitrogen of each amino acid is blocked with Fmoc (9-fluorenylmethoxycarbonyl). Three equivalents of the C-terminal amino acid are added to 1 equivalent of Wang resin (p-benzyloxybenzyl alcohol attached to a polystyrene resin) in the presence of N,N-dicyclohexylcarbodiimide to form the anhydride. Following coupling of the first amino acid, any unreacted groups on the resin are blocked by treatment with excess benzoic anhydride. For each subsequent amino acid addition to the peptide, the Fmoc group is first removed from the nascent peptide-resin complex with 15% piperidine in N-methylpyrrolidone. Coupling is performed by activation of the carboxyl groups of the N-protected amino acids with 3 mol/mol 2-(1H-benzotriazol-1-yl)-1,1,3,3-tetramethyluronium tetrafluoroborate/1-hydroxybenzotriazole in combination with DIPEA (diisopropylethylamine) in NMP. Activated amino acids are sequentially added to the nascent peptide and mixed for 30 minutes. The extent of coupling is estimated by performing a ninhydrin assay (Kaiser test) on a few resin beads to detect remaining unreacted amines. Side chain protecting groups are as follows. The guanidino function of arginine, R, is protected by 2,2,7,8-pentamethylchroman-6-sulfonyl (Pmc)), the ?-amino groups of lysine (K) by t-butyloxycarbonyl (Boc), the carboxamides of asparagine (N) and glutamine (Q) and the thiol of cysteine by trityl (Trt) and carboxyl groups of glutamic and aspartic acids as well as the hydroxyl groups of serine, threonine and tyrosine by t-butyl.

Upon completion of the synthesis, the peptide-resin is vacuum dried and cleaved and deprotected by stirring 3 hours in a solution containing 95% trifluoroacetic acid, 1% crystalline phenol, 1% ethanedithiol, 2% ml thioanisole in distilled water. The mixture is filtered through glass wool directly into ice cold diethylether. The peptide precipitate is washed several times with additional ether and dried. Final purification is carried out by reversed-phase HPLC on a C8 or C18 column. The purity of all synthetic peptides is ascertained by reversed phase HPLC on a C18 column typically employing a water/acetonitrile gradient in the presence of 0.1% trifluoroacetic acid. Identity is verified by MALDI-TOF mass spectrometry and by amino acid composition employing a Waters Pico-Tag System or, if necessary, by N-terminal sequence analysis. Peptide content is determined by quantitative amino acid analysis.

3H Thymidine assay. In particular the tritiated thymidine assays were performed as follows. 10,000 cells were plated in 1 ml of RPMI 1640 medium containing 10% fetal bovine serum in 24-well plates. The cultures were incubated for 24 hours at 37 C, 5% carbon dioxide. The peptide was added to each corresponding well at different doses and allowed to incubate for 72 hours. The cells were then exposed to tritiated thymidine at a concentration of 1 uCi/ml (ICN, cat #2403905) and incubated at 37 C for 4 hours. The cells were washed twice with cold PBS to remove non-incorporated thymidine. The cells were treated twice with 10% trichloracetic acid (Fisher, lot #94276913), 1 ml per well. The cells were then disrupted by treatment with 10% sodium lauryl sulfate (Sigma, Cat #L-3771) at 500 ul/well. Cell from each well were transferred to a scintillation vial and counted in a Beckman Counter Model LS-133 scintillation counter.

XTT method. A commercial (Roche, N.J.) kit was used. At the end of the experiment the XTT labeling mixture was coupled to the electron reagent coupling and was added to the cultured cells in microplate for 4 hours. The microplate was placed in an ELISA microplate reader (Molecular devices, Menlo Park, Calif.).

Mitochondrial membrane potential. A stock solution of JC-1 dye (100 μg/ml in DMSO) is prepared. Cells are preincubated with the peptide of SEQ ID NO: 2 for up to 24 hours. JC-1 reagent is diluted just prior to use. For each assay, 100 μl of stock solution is diluted to 1 ml using pre-warmed cell culture medium and the solution is vortexed. 40 μl of diluted JC-1 is added to each well and incubated at 37° C. in 5% $CO_2$ incubator for 25-30 min. Medium is replaced with pre-warmed PBS. Samples are detected by fluorescent signals by using flow cytometry results compared to buffer only treated controls. JC-1 reagent accumulates in the intact mitochondria, giving off a bright red fluorescence. In apoptotic cells, JC-1 reagent cannot accumulate in the mitochondria due to the altered mitochondrial membrane potential.

Western blot performed with IgY. The materials used included: Tris-buffered Saline-Tween 20 solution (TBS-T): 1.21 g Tris-base (10 mM), 8.77 g NaCl (150 mM) NaCl, in 1 L of H20, pH 7.4, containing 0.05% (v/v) Tween-20; non-fat dry milk; a GenWay Immunoblotting blocker reagent; HRP-conjugated goat anti-IgY Fc antibody (GenWay Catalog#: GAYFC-HRP) and the Immun-blot colorimetric assay kit (Bio-Rad).

An appropriate amount of cell lysates (1-10 ul of 0.5 mg/ml each lane) was separated using a 10-20% SDS-PAGE, followed by transfer to PVDF membrane. The membrane was blocked with 5% non-fat milk in TBS-T (Tris-buffered saline containing 0.05% Tween, pH 7.4) for 1 hour at room temperature or longer at 4° C. (BSA is not recommended as a blocking reagent). The membrane was rinsed with TBS-T and incubated with IgY antibodies at an appropriate dilution with milk to 1% in TBS-T at room temperature (RT) for 1 h. Optionally the membrane can be pre-incubated with IgY diluted with GenWay Immunoblotting blocker at RT for 1 h prior to submerging the membrane. This step may help to reduce background, especially when *E coli*-derived antigen is used. The membrane is washed with TBS-T, 3 min each, a total of 3 times, followed by incubation with the $2^{nd}$ antibody (goat-anti-IgY/Fc-HRP) at a dilution of 1:1,000 for colorimetric assay or 1:10,000-1:100,000 for ECL (with 1% milk TBS-T) at R.T. for 1 h. The membrane is then washed with TBS-T, 3-5 min each with shaking, total of 3 times. Color development is performed or ECL detection of the signal using Pierce ECL kit.

EXAMPLE 2

HPLC Purified Developmental Peptides Potent Antiproliferative Effects

HPLC, RP HPLC, etc, for example, provides for isolation of highly purified developmental peptides that have potent antiproliferative effects. The activity of purified developmental peptides <3000 Da, purified by HPLC, was shown to affect several aspects of proliferation. Similar effects were noted also with <10,000 dalton developmental peptides. Developmental peptides <3000 Da from porcine liver induce apoptosis and activate caspases activity of preneoplastic breast cancer cells. Developmental peptides also cause mitochondrial collapse with the release Cytochrome C in MCF10neo cells. In all cases developmental peptides had over 63% inhibition of cell proliferation compared to controls.

Developmental peptides <3000 Da also inhibit 99% 3H thymidine incorporation into cellular DNA of a pre-neoplastic cell line (MCF10neo cells) in a dose dependent manner. The EC50 is about $\frac{1}{13}^{th}$ Dpa dilution.

Developmental peptides <3000 Da from porcine liver exert a major inhibitory effect on resistant prostate cancer cell lines (DU145, androgen receptor negative resistant) causing apoptosis, as evidenced by three different models of flow cytometry: a TUNEL assay, caspase activity as determined by cell permeability using flurogenic $D_2R$ substrate, and mitochondrial permeability transition assessed by $DiOC_6$ staining. With the first two methods >95% inhibition was noted compared to controls.

FIG. 1 shows that developmental peptides are also highly effective against a surgical specimen of renal cancer cells that is highly resistant to chemotherapy. Cells were incubated with purified developmental peptides for approximately 24-30 hrs. While developmental peptides were effective in inhibiting proliferation of the renal cancer cells, two standardly used chemotherapies (a 5-FU regimen and a vinblastine regimen) remained ineffective, even at a high concentrations of approximately 10-100 fold.

Overall, developmental peptides exhibited an antiproliferative activity against an array of early stage to resistant cancer cell lines, steroid receptor positive or negative, and actual patient tumor cells. The effect on cell proliferation was observed using 3H thymidine, XTT, JC-1 (for mitochondrial collapse assay), PI staining, and apoptotic pathways in both a time and dose dependent manner with at least >70% reduction in cell survival, as documented by flow cytometry as well as by microphotomicrographs.

Figure 2:
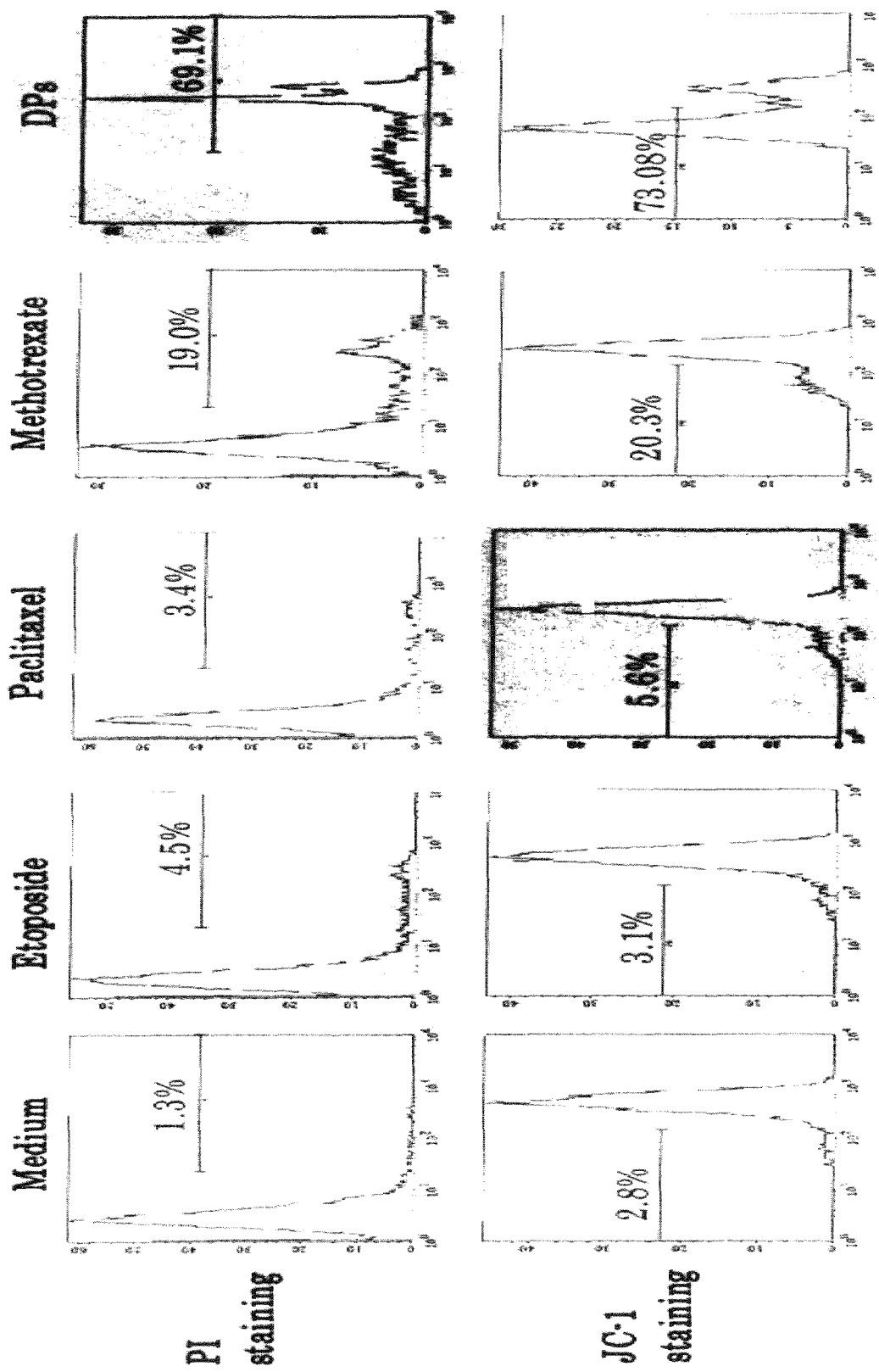
FIG. 2 shows that cells isolated from renal cancer specimen were completely inhibited by addition of highly purified adult porcine liver derived developmental peptides <3000 kDa. In contrast, other types of chemotherapy even in high doses had no effect. PI and JC-1 staining both shows >70% inhibition, while the most effective chemotherapy effect was 20%.

Exposure of the cells to developmental peptides caused a 99% inhibition of proliferation, in comparison to chemotherapy, which had only a marginal effect. FIG. 2 further confirms developmental peptides effectiveness as compared to chemotherapy. Short-term cultured renal carcinoma cells (RCC) were incubated with developmental peptides. Analysis of cell viability using PI staining revealed that there was a profound loss of cell viability. It should be noted that conventional chemotherapeutic agents, such as etoposide, paclitaxel, and methotrexate for example, failed to induce cell death in the RCC cell lines. While not wishing to be bound to theory, the anti-proliferative effect of developmental peptides is thought to be due to the developmental peptides induction of mitochondrial alterations in the malignant cells, as analyzed using JC-1 staining, a process which invariably leads to cell death. Preincubation of DU-145 cells, a human prostate cancer cell line, with non-lethal concentrations of developmental peptides increased the prostate cell sensitivity to cell death if subsequently stimulated with either TNF-α or paclitaxel. Thus, low concentrations of developmental peptides may enhance the efficacy of a chemotherapy regimen.

Figure 3:
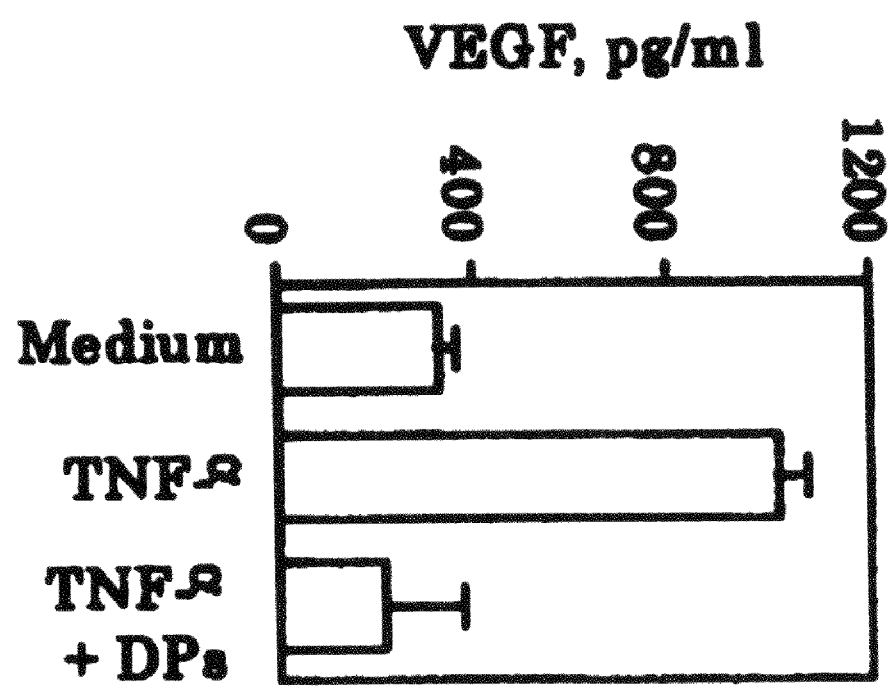
FIG. 3 illustrates the anti-angiogenic effect of highly purified developmental peptides <3000 daltons isolated from adult porcine liver upon resistant androgen prostate cancer cells (PC3). developmental peptides blocked VEGF expression by cancer cells. This complements the block of expression of NF kB in these cells (data not shown).

FIG. 3 illustrates that developmental peptides have a wide range of antiproliferative activity, showing NFkβ inhibition and inhibiting angiogenic factor VEGF secretion by prostate cancer cells. Developmental peptides drastically reduced VEGF expression by PC-3 prostate cancer cells in vitro. Developmental peptides suppress NF-kβ activity and VEGF expression in prostate cancer cells, thereby inhibiting their tumorigenic and metastatic properties in vitro and in vivo. Developmental peptides may diminish the angiogenic and metatstatic potentials of prostate cells via down-regulation of NF-kβ regulated molecules, such as, but not limited to, VEGF, IL-6, IL-8, and MMP-9.

Figure 4:
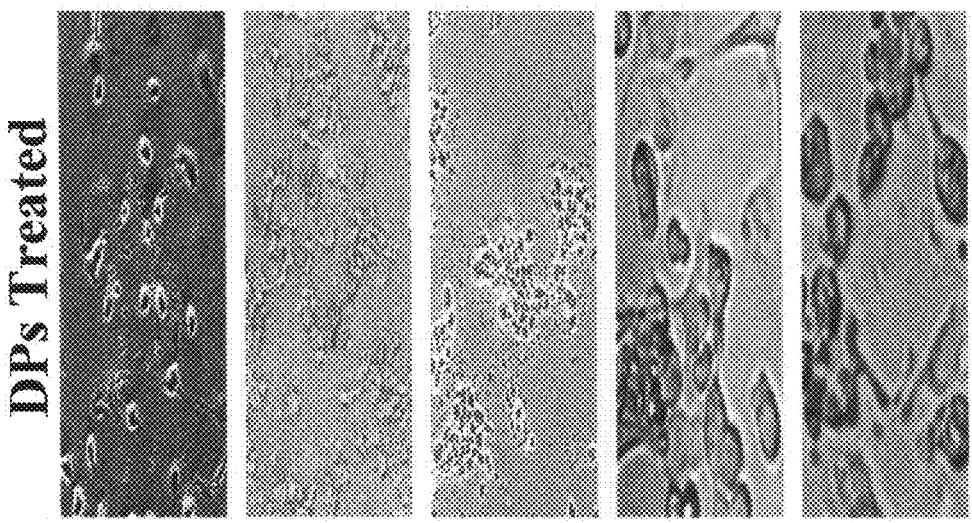
FIG. 4 shows microphotographs comparing the effects of highly purified <3000 daltons developmental peptides derived from adult porcine liver compared to controls. Images shows that in all cases, preneoplastic breast, prostate, patients renal cancer exposure to developmental peptides causes practically collapse of the cell, without extrusion of the cellular content, a significant reason for chemotherapy induced toxicity.

FIG. 4 illustrates that developmental peptides cause shrinking (implosion) and loss of cell to cell contact of various cancer cell lines. A similar effect was also observed using metastatic fallopian tube cancer cells (99% inhibition dose dependent).

EXAMPLE 3

Antiproliferative Effects of Synthetic Developmental Peptides

HPLC, RP HPLC, and other non limiting methods can be used for identifying developmental peptides in different tissues. The presence, isolation and characterization of one of the anti-proliferative peptides present in the active fraction was documented in both the adult and fetal porcine liver (SEQ ID NO: 2). A mass spectral profile of porcine embryonal liver extract revealed a number of peptides with a 970-1230 dalton mass. The 970 dalton developmental peptide was sequenced using the Qstar Mass Spec method and its sequence was found to be novel, confirming the findings in adult liver. The partial characterization of potent developmental peptides at the 3-10 kDa region using fresh liver tissue is described as well. Present results show that developmental peptides are relevant both for adult and developing tissues and their presence can be documented in several species making these observations universal for all mammals. Thus the size of the peptides/protein are at about 500-10,000 Da region. The actual sequence derived shares homology with a portion of an endogenous retrovirus (FIG. 5). However, the methods described herein allow for the identification of other protein or peptides that have antiproliferative activities.

The role of developmental peptides appears to be of high relevance, since they are produced both in the embryo as well as in the adult liver. As an example showing the wide spread developmental peptides effect when only one compound is involved, confirmed that actually single agents may have the antiproliferative activity and therefore there is no need for using mixtures or only the animal source.

A breast cancer cell line (MCF-7) and human mammary epithelial cells (HMEC) were incubated with the 9 AA developmental peptides of SEQ ID NO: 2. 3H thymidine labeling of DNA was used to analyze the anti-proliferative effect of developmental peptides using concentrations in the range of about 1.5-12 mg/ml developmental peptides. An antiproliferative response was maintained on the breast cancer cell line (MCF-7 cells) using low concentrations of developmental peptides in the absence of any harmful or negative effect on the normal HMEC cells. The antiproliferative response was repeated and analyzed using the XTT method. Again the 9 AA developmental peptides, at low concentrations of about 1.5 mg/ml, maintained the antiproliferative effect on MCF-7 cells with minimal effect on the HMEC cells. Finally, this same analysis was repeated using resistant prostate cancer cells, the PC3 cell line, which are androgen receptor negative cells. Developmental peptides was added to the cells using concentrations of about 6-25 mg/ml for 24 hours in the presence of 3H thymidine to measure the effect of developmental peptides on cell proliferation. As seen with the breast cancer cell line (MCF-7), the 9 AA developmental peptides also had an antiproliferative effect (approximately 98% inhibition) on the resistant prostate cancer cell line at concentrations in the range of about 12-25 mg/ml. These results were further confirmed using the XTT method, by direct microscopic observations, and by JC-1 staining to detect mitochondrial collapse, and further confirmed by flow cytometry.

EXAMPLE 4

Antibodies Against Developmental Peptides

Antibodies against developmental peptides may be produced and purified. Antibodies against a nine amino acid developmental peptide of SEQ ID NO: 2 (IgY, generated in chicken) were affinity purified on a column containing pure developmental peptides. The antibodies generated were used as biomarkers for determining the expression in various mammalian tissues. Developmental peptides IgY is highly specific and results in the intense staining of the human pancreatic exocrine portion (epithelial cells) of pancreatic tissue in the absence of binding to the endocrine portion of the pancreas (Langerhans cells). The staining was specific in that binding of antibody to tumor cells was neutralized by addition of the developmental peptides. Also, a control IgY was ineffective in binding to tumor cells. In contrast, the normal liver staining was essentially negative. Developmental peptide IgY binds normal tissue only very weakly in the epithelial glandular layer of various tissues, such as prostate, fallopian tube, and stomach, colon epithelium in human and mouse tissue arrays in a non limiting manner. No binding to the liver tissue was detected. Other tissues of normal human and mouse did not bind to developmental peptide IgY. The presence of developmental peptides in epithelial cells reflect a strategic localization of the nine amino acid developmental peptides and related proteins in cells that are most liable to become malignant (that is, those cells that are normally proliferating), and thus may create homeostasis by counteracting local growth factors. Altered proliferation may become a cancer under the influence of mitogens, carcinogen, or altered gene expression is prevented.

Evidence that the nine amino acid developmental peptides antibody reflects staining of specific proteins as shown by Western blot. Human placental extracts, as well as the pancreas and liver, expressed developmental peptides of SEQ ID NO: 2 related pro-proteins, confirming that the immunohistochemistry actually reflects expression of developmental peptides and related proteins. The developmental peptide IgY stained the hepatocarcinoma sample in contrast to normal liver (which was negative). This increased staining was confirmed in several human tumors from almost all organs. Anti-developmental peptide IgY specifically binds to adult human bladder cancer tissue, adult human lung carcinoma tissue, cervical cancer, and endometrial carcinoma tissue with almost no binding to normal endometrium. The Western blot pattern in placental, pancreas and liver tissue lysates revealed expression of protein bands about 20-40 kDa, similar to the human placenta, pancreas and normal liver. However, the first trimester blot contained only one band at about 15 kDa region, indicating differential expression during pregnancy. The pattern detected in liver cancer revealed high molecular weight (40-140 Da) proteins that does not match any observed in normal liver or pancreas, while the 32 kDa size protein was attenuated in cancer. Altered proteolytic processes that impair active developmental peptide formation may contribute to the tumor pathogenesis.

Overall, generation of the IgY antibody documented by two independent methods demonstrate that developmental peptide related proteins and peptides are differentially expressed in tumors compared with normal tissues. Discovery of the altered protein synthesis and degradation may be of high relevance for understanding tumor propensity in that the great majority of cases of tumorigenesis are of epithelial origin. Additional observations using the tumor array revealed that in almost all instances there was an intense staining of the blood vessels, which are known to proliferate intensely although aberrantly during malignancy, is further documentation that the antibody targets rapidly dividing cells. The blood vessels are the prime source of nourishment and growth of the tumor. Indeed, lack of vascularity greatly limits the ability of the tumor to grow beyond a certain size. Thus, both the epithelium and the blood vessels appear to be the major sites where the expression of developmental peptides, including the developmental peptides of SEQ ID NO: 2, and related proteins are responsible for control of proliferation. A detailed observation of the microphotograph also documents that the antibody binds practically only to the cytoplasmic region of the cells.

EXAMPLE 5

Developmental Peptide Receptors

The developmental peptides and related molecules act through specific sites of action which may be located within the cell and are selectively activated by cellular transformation. This is shown by lack of uptake of FITC developmental peptides by normal rat embryos in culture. In contrast, the labeled developmental peptides bound to embryonic tissue receptors following exposure to mutagen, such as for example 5FU. This indicates that the receptor for developmental peptides exists in embryonic tissues however it becomes accessible to the peptide only when there is exposure to a mutagen/carcinogen. Thus, the production of developmental peptides occurs in embryonic tissues as well where the target organs are local but are only activated, in the case of exposure to an adverse environment, thereby protecting and likely eliminating only abnormal cells through apoptosis or non apoptotic pathways without affecting normal cells. Therefore the use of developmental peptides could identify and characterize such receptors leading to their cloning and expression. This could be achieved by using enriched membranes where the receptor is highly expressed (embryos following exposure to 5FU, as a non limiting example) followed by using an affinity chromatography containing a Biotin labeled developmental peptides column followed by mass spectometry and sequencing. In addition, characterization of the receptor could lead to the identification of the specific intracellular mechanism and the transduction molecules that create cell death, thereby revealing fundamental properties that the abnormal cells possess that create an integrated response to the presence of the developmental peptides overcoming resistance to cell death that is seen with chemotherapy. These new and integrated transduction mechanisms identified could lead to further development and design of new pharmacophores and targeted drugs.

Since one aim may be to develop cancer drugs targeted for human therapy and since the human pancreas and placenta shared similar protein pattern as observed by Western blot, an affinity chromatography using the developmental peptide IgY column was designed. The protein profile in the liver cancer sample was different as compared to normal tissues, which may be due to abnormal synthesis, processing, and/or degradation. High molecular weight proteins were exclusively found in the liver tumor (approximate MW of 140, 90, 60) with attenuation of the 30 kDa band. A number of proteins were identified by mass spec analysis of non-denatured human placental tissue extracts using the developmental peptide IgY antibody. The major protein observed was 32 kDa, similar to that seen by Western blot. The partial sequence and comparison with known protein using mass spec based sequencing revealed that the major protein may be attached to non muscle actin (gamma actin) and to a portion of RNA polymerase molecule, both of which are known to interact with HERV. Further analysis of the <10 kDa region revealed that the major protein may be a portion of HERV (gag, or env portion) confirming the earlier observations with the developmental peptides of SEQ ID NO: 2 homology to HERV pol. Thus, in the placenta the developmental peptides appear to be attached to the cytoskeleton of the cells which are located in the cytoplasm of the cell. Such observations suggest a linkage between cell proliferation and cytoskeleton architecture, and cell mobility and implicates the developmental peptide as a likely partner in regulating cytoskeleton function which is altered in malignancy and following viral infection. This data further documents that HERVs are likely to have multiple roles beyond the immune suppression identified to date.

Thus, the methodology described allows for the isolation of cellular proteins and possibly other transcription factors and regulatory agents that are operative during development as well as in the adult and are present mainly in epithelial cells. The method described also allows for identification of various proteins that are over-expressed in cancer cells and tissues and others that are suppressed using, for example, Western blot, 2 D gel electrophoresis, Mass spectometry, and affinity chromatography as described in a non limiting manner.

The data generated allows further separation of the large proteins from the cytoskeleton elements to derive the active developmental peptides that are expected to have a major anticancer effect approximately 1000 fold greater than the effectiveness of the developmental peptides of SEQ ID NO: 2 and which could be used for the prevention and treatment of proliferative disorders as well as diagnosis of such disorders. In addition, identification of specific interacting factors with developmental peptides can be applied for both diagnostic and therapeutic application by using the compounds themselves or by generating antibodies to test for those in tissues and biological fluids in a non-limiting manner.

In a further examples, <10 kDa adult porcine liver developmental peptides also have antiviral effects as shown by protection against cell death of MRC-5 human fibroblasts that were infected with cytomegalovirus. These observations were documented by light microscope as well as by XTT and X-Gal methods, the effect being dose dependent. This further substantiates earlier observations made in a previous application where a wide range of antiviral effects were noted with high molecular weight developmental peptides and low molecular weight (<8000 Da) developmental peptides with an HBL-100 cell line transformed with SV-40 viral protein. In addition, <10,000 kDa had significant dose dependent protective effects on Hep2 cells in culture that were exposed to respiratory syncitial virus (RSV). Protective effects were also found against vaccinia virus (a small pox homologue). Pre-incubation with <10 kDa developmental peptide results in an almost complete protection against viral infection.

Extraction of the lipids from the <3 kDa fraction did not have an effect on developmental peptide antiproliferative activity. In addition, the porcine liver 3-10 kDa fraction was separated on an organomercurial agarose gel to determine if the developmental peptides have free sulphydrils. The developmental peptides retained their anticancer activity indicating that developmental peptides do not have free sulphydrils.

Using specific inhibitors the mechanisms by which developmental peptides block MAPkinase was examined. It was found that the ras-raf pathway, IP3 kinase, and src kinase and tyrosine phosphatases are involved in developmental peptide action. The transmembranal tyrosine kinase, and PKC do not appeared to be involved. Also based on additional experiments developmental peptide action is not exerted through TNF-α, TRAIL or CD95 pathways.

Since developmental peptide binds only abnormal cells in the embryo a FITC-labeled developmental peptides method could be used for screening of teratogens/mutagens. This method could identify potential teratogens/mutagens and allow for their removal from the environment, thus preventing exposure of the fetus to the teratogen/mutagen, preventing an adverse pregnancy. In addition, such a method could be used to assess various compounds that are being developed as drugs and therefore using as a rapid screening method to determine which of these drugs could be least likely to have a toxic effect while maintaining its potential therapeutic profile.

EXAMPLE 6

Sequence Analysis of Human Protein Database

A blast search was performed Val-Leu-Gly-Lys-Arg-Ile-Lys-Gly-Thr (SEQ ID No.2) versus the human protein database. Table 1 illustrates the human protein matches. Table 2 illustrates the amino acid distribution frequency across aligned sequences and upstream/downstream sequences for the matches.

TABLE 1

SEQUENCING OF THE >10 Kd MW SIZE DP PROTEINS USING LC/MASS SPECTRUM METHOD

| Scan(s) | m/z | Charge | Sequence | Reference | Database | X-Corr | Delta Cn | Sp | RSp |
|---|---|---|---|---|---|---|---|---|---|
| 113 1461-1468 | 1791.956 | 2 | -.SYELPDGQVITIGNER.F | gi\|998467\|gb\|AAB34251.1 | human_0-10kD.fast | 3.913 | 0.712 | 1336.3 | |
| 88 1348-1358 | 946.137 | 2 | R.AVFPSIVGR.P | gi\|998466\|gb\|AAB34252.1 | human_0-10kD.fast | 2.322 | 0.668 | 607.8 | |
| 95 1364 | 1956.206 | 2 | K.LKEQYVNKTIVFNQSSG | gi\|4580115\|gb\|AAD24254. | human_0-10kD.fast | 2.147 | 0.532 | 183.4 | |
| 97 1366-1380 | 1958.138 | 3 | K.SDVVQIDNNKNYTKYR. | gi\|857635\|gb\|AAC54509.1 | human_0-10kD.fast | 1.789 | 0.122 | 172.4 | |
| 65 1252-1276 | 1906.186 | 3 | K.AAYLQETGKPLDETLKK | gi\|6729710\|pdb\|1BO9\|A | human_0-10kD.fast | 1.733 | 0.249 | 314.9 | |
| 111 1448-1456 | 1959.169 | 2 | -.CTNANVGNM#DTEM#V | gi\|3065485\|gb\|AAC61162. | human_0-10kD.fast | 1.656 | 0.022 | 359.6 | |
| 87 1333-1349 | 1842.019 | 3 | R.RAEPAADGVGAVSRDL | gi\|424402\|gb\|AAA44246.1\| | human_0-10kD.fast | 1.519 | 0.250 | 667.9 | |
| 459 3190 | 1853.155 | 3 | -.DRLHPVHAGPIAPGQMR. | gi\|4098015\|gb\|AAD00191. | human_0-10kD.fast | 1.480 | 0.323 | 143.0 | |
| 78 1296-1302 | 1905.034 | 3 | R.GLVLATNNQDNPHPQG | gi\|485020\|pir\|\|PQ0548 | human_0-10kD.fast | 1.449 | 0.208 | 446.5 | |
| 578 3441-3465 | 1968.259 | 3 | R.AFYASRQIIGDMRQAHC | gi\|415141\|gb\|AAA44354.1\| | human_0-10kD.fast | 1.445 | 0.202 | 70.3 | |
| 175 1745-1752 | 1980.363 | 3 | R.VLAEAMSQVQNAAIMM | gi\|3462724\|gb\|AAC33060. | human_0-10kD.fast | 1.444 | 0.060 | 310.3 | |
| 533 3341-3369 | 1938.174 | 3 | R.AYCNVNRAAWNETLRR | gi\|15429907\|gb\|AAK98388 | human_0-10kD.fast | 1.438 | 0.045 | 27.0 | |
| 100 1382 | 1955.178 | 2 | K.LREQFNXTTIVFNQSSG. | gi\|8489575\|gb\|AAF75719. | human_0-10kD.fast | 1.427 | 0.243 | 85.9 | |
| 461 3193 | 1858.250 | 3 | K.VIIVQLNETVQIKCTR.P | gi\|2570736\|gb\|AAB82244. | human_0-10kD.fast | 1.415 | 0.378 | 92.0 | |
| 633 3536-3572 | 1311.389 | 3 | R.AFNC*HVEYEK.T | gi\|10720143\|sp\|O95158\|N | human_0-10kD.fast | 1.395 | 0.154 | 161.2 | |

| | Reference | Score | Hits | Entries |
|---|---|---|---|---|
| 1 | gi\|6435104\|gb\|AAF08451.1\|(AF152813) envelope protein [Human immunodeficie | 20.0 | 20000 | 603 630:::: |
| 2 | gi\|11875564\|gb\|AAG40705.1 | 20.0 | 20000 | 89 481:::: |
| 3 | gi\|998468\|gb\|AAB34252.1\|48 kda histamine receptor subunit peptide 1 {inte | 20.0 | 20000 | 88 90:::: |
| 4 | gi\|1703643\|gb\|AAB37684.1\|laminin alpha 2-chain short arm {cysteine-rich r | 18.0 | 11000 | 541:630::: |
| 5 | gi\|3462724\|gb\|AAC33060.1\|(AF082448) gag protein [Human immunodeficiency v | 16.0 | 10100 | 175::175:: |
| 6 | gi\|10863925\|ref\|NP_066951.1\|(NM_021128) DNA directed RNA polymerase II po | 14.0 | 12411 | :578:578:: |
| 7 | gi\|7245807\|pdb\|1DV0\|A Chain A, Refined Nmr Solution Structure Of The C-Ter | 14.0 | 11100 | :95:97:: |
| 8 | gi\|4580121\|gb\|AAD24257.1\|(AF095023)envelope glycoprotein [Human immunode | 12.0 | 10002 | 475::::572 |

TABLE 2

AMINO ACID RESIDUE DISTRIBUTION FREQUENCY ACROSS ALIGNED SEQUENCES AND UPSTREAM/DOWNSTREAM SEQUENCES

| | | | | | | | V | L | G | K | R |
|---|---|---|---|---|---|---|---|---|---|---|---|
| 1 Peptide sequence 2 Residue | Pos1 | Pos2 | Pos3 | Pos4 | Pos5 | Pos6 | Pos7 | Pos8 | Pos9 | Pos10 | Pos11 |
| 3 A | 8 | 0 | 1 | 2 | 3 | 0 | 5 | 0 | 9 | 0 | 0 |
| 4 C | 2 | 1 | 0 | 0 | 0 | 2 | 0 | 2 | 1 | 0 | 0 |
| 5 D | 4 | 5 | 5 | 5 | 3 | 0 | 1 | 0 | 1 | 0 | 0 |
| 6 E | 1 | 9 | 4 | 3 | 3 | 3 | 3 | 1 | 1 | 0 | 0 |
| 7 F | 2 | 3 | 4 | 2 | 2 | 1 | 4 | 0 | 1 | 0 | 0 |
| 8 G | 1 | 5 | 3 | 3 | 9 | 0 | 1 | 0 | 25 | 0 | 1 |
| 9 H | 3 | 3 | 0 | 2 | 4 | 2 | 2 | 0 | 0 | 0 | 0 |
| 10 I | 0 | 1 | 2 | 7 | 4 | 3 | 6 | 2 | 0 | 0 | 1 |
| 11 K | 4 | 3 | 2 | 4 | 1 | 3 | 2 | 0 | 0 | 43 | 4 |
| 12 L | 7 | 1 | 4 | 2 | 7 | 0 | 2 | 38 | 2 | 0 | 0 |
| 13 M | 1 | 2 | 1 | 1 | 1 | 2 | 0 | 2 | 0 | 0 | 0 |
| 14 N | 0 | 1 | 2 | 3 | 2 | 3 | 1 | 0 | 1 | 0 | 0 |
| 15 P | 2 | 1 | 4 | 1 | 3 | 7 | 2 | 1 | 0 | 1 | 0 |
| 16 Q | 1 | 5 | 3 | 3 | 3 | 5 | 1 | 2 | 0 | 0 | 1 |
| 17 R | 1 | 1 | 3 | 1 | 1 | 3 | 0 | 0 | 1 | 4 | 41 |
| 18 S | 6 | 3 | 4 | 3 | 0 | 3 | 4 | 1 | 6 | 1 | 0 |
| 19 T | 3 | 2 | 1 | 2 | 0 | 3 | 2 | 0 | 0 | 0 | 0 |
| 20 V | 1 | 2 | 4 | 4 | 3 | 7 | 12 | 0 | 0 | 0 | 1 |
| 21 W | 2 | 0 | 0 | 0 | 0 | 1 | 1 | 0 | 1 | 0 | 0 |
| 22 Y | 0 | 1 | 2 | 1 | 0 | 1 | 0 | 0 | 0 | 0 | 0 |
| 23 | | | | | | | | | | | |

TABLE 2-continued

AMINO ACID RESIDUE DISTRIBUTION FREQUENCY ACROSS ALIGNED SEQUENCES AND UPSTREAM/DOWNSTREAM SEQUENCES

| 1 Peptide sequence<br>2 Residue | I<br>Pos12 | K<br>Pos13 | G<br>Pos14 | T<br>Pos15 | Pos16 | Pos17 | Pos18 | Pos19 |
|---|---|---|---|---|---|---|---|---|
| 3 A | 0 | 0 | 3 | 2 | 2 | 4 | 2 | 4 |
| 4 C | 0 | 0 | 1 | 0 | 1 | 1 | 1 | 0 |
| 5 D | 0 | 2 | 2 | 1 | 1 | 3 | 5 | 2 |
| 6 E | 1 | 1 | 0 | 3 | 1 | 8 | 3 | 1 |
| 7 F | 1 | 0 | 0 | 3 | 3 | 1 | 0 | 0 |
| 8 G | 0 | 2 | 11 | 1 | 9 | 6 | 4 | 7 |
| 9 H | 0 | 0 | 0 | 0 | 2 | 1 | 3 | 1 |
| 10 I | 36 | 2 | 1 | 8 | 5 | 0 | 3 | 6 |
| 11 K | 0 | 32 | 1 | 4 | 5 | 8 | 3 | 3 |
| 12 L | 5 | 0 | 1 | 3 | 2 | 1 | 6 | 3 |
| 13 M | 0 | 1 | 1 | 2 | 0 | 1 | 0 | 1 |
| 14 N | 0 | 3 | 2 | 1 | 1 | 1 | 0 | 2 |
| 15 P | 0 | 0 | 2 | 0 | 1 | 3 | 4 | 0 |
| 16 Q | 0 | 0 | 2 | 1 | 1 | 2 | 2 | 3 |
| 17 R | 0 | 5 | 7 | 8 | 0 | 3 | 1 | 1 |
| 18 S | 0 | 1 | 2 | 3 | 5 | 3 | 7 | 6 |
| 19 T | 1 | 0 | 1 | 7 | 4 | 2 | 1 | 4 |
| 20 V | 4 | 0 | 11 | 1 | 3 | 0 | 1 | 5 |
| 21 W | 0 | 0 | 0 | 0 | 2 | 0 | 1 | 0 |
| 22 Y | 1 | 0 | 1 | 1 | 1 | 1 | 2 | 0 |
| 23 | | | | | | | | |

Table 2 is the amino acid distribution frequency across aligned sequences and upstream/downstream sequences for the human protein database matches.

EXAMPLE 7

Binding of Developmental Peptides to Abnormal Embryo

Figure 6:
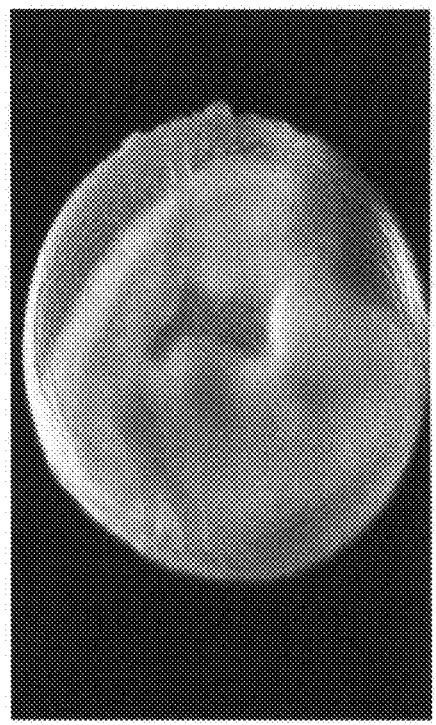
FIG. 6 shows that synthetic developmental peptides (9aa) are not teratogenic when added to rat embryo cultures for 48 hours, using the roler bottle system.

Rat embryo cultures were exposed to synthetic developmental peptides of about 9 AA (about 500 μg/ml) for 48 hours (FIG. 6). The viscera yolk sac and the embryo both developed normally. Thus, the developmental peptides of the present invention are not teratogenic.

Figure 7:
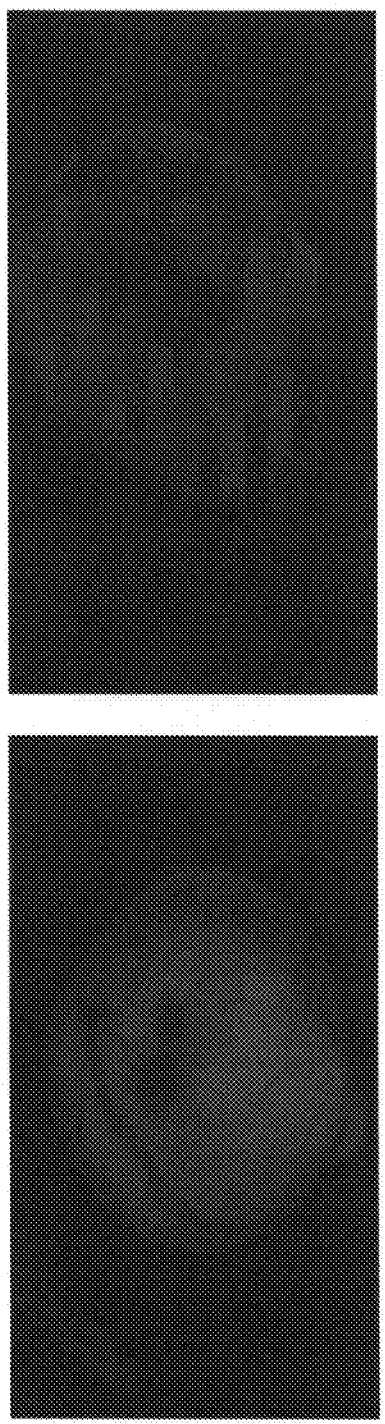
FIG. 7 shows that exposure of FITC-developmental peptides to rat embryos cultured in roler bottles for 48 hours was not associated with uptake by the tissue of the peptides.
Figure 8:
FIG. 8. In contrast, exposure to 5FU (a potent teratogen/chemotherapeutic agents) for 3 hours led to major uptake of FITC-developmental peptides by the various tissues. This indicates expression of development peptides receptor only when the embryo is exposed to a teratogen/mutagen.

Whole rat embryos (within the amniotic sac) were exposed to FITC-developmental peptides for 48 hours (FIG. 7). There was no uptake of peptides by the tissue. In contrast, when the rat embryo's were grown in normal serum and exposed to +/−5-FU (a potent teratogen/chemotherapeutic agent) for 3 hours (FIG. 8), followed by exposure to FITC-developmental peptides for 48 hours. Fluorescent stereomicroscopy revealed that the fluorescent-developmental peptides accumulated in the tissues. This result reveals that developmental peptides bind only to specific receptors that are present or have been activated on damaged embryos. In this example the damage was due to exposure to the 5-FU, a potent teratogen/chemotherapeutic agent. Under normal conditions the receptors remain non-active.

EXAMPLE 8

Binding of Developmental Peptides to Proliferating Cells of First Trimester Placenta The 9 AA developmental peptide IgY antibody identifies proliferating cells. First trimester placenta was cultured on Matrigel and stained with anti-developmental peptide IgY. Anti-developmental peptide antibodies bind specifically to the proliferating cells in the first trimester placenta, this binding is accentuated after 96 hours of culture.

Examination of the first trimester placenta, after exposure to anti-developmental peptides IgY, revealed that only the proliferating cells of the extravillous trophoblast (EVT) were bound by anti-developmental peptides antibodies. The EVT cells also have a high invasive potential, however they stop proliferating once adequate contact with the maternal endometrium is well established. Developmental peptides may serve to limit such invasivity in vivo. The first trimester placental extracts were stained with anti-HSP27 and anti-Ki27, antibodies that detect the corresponding HSP27 and Ki27, two proliferation markers. The anti-HSP27 and anti-Ki27 antibodies bound specifically to the proliferating cells, confirming the specificity of the anti-developmental peptide antibody which also bound to the proliferating cells only.

First trimester explants were exposed to either anti-developmental peptides and anti-HSP27 antibodies or to anti-developmental peptides and anti-Ki27 antibodies. The HSP27 and Ki27 proliferation markers were observed to co-localize with developmental peptides in placental explants. This confirms the role of developmental peptides as a negative regulator of placental proliferation, possibly by directing cells toward differentiation instead of proliferation and invasivity, neoplastic-like properties.

Western blot analysis of normal adult and placental tissue were probed with affinity purified developmental peptide IgY (1:500) followed by goat ant-IgY HRP antibody 1:1000. The results revealed that term placenta, pancreas and liver patterns were similar. Normal and cancerous liver extracts were also analyzed by Western blot (using the same antibodies) The results revealed that the 9 AA developmental peptide antibodies identified an altered pattern of developmental peptide expression in the cancerous tissue sample.

What has been described and illustrated herein are embodiments of the invention along with some of their variations. The terms, descriptions and figures used herein are set forth by way of illustration only and are not meant as limitations. Those skilled in the art will recognize that many variations are possible within the spirit and scope of the invention, which is intended to be defined by the following claims and their equivalents in which all terms are meant in their broadest reasonable sense unless otherwise indicated.

What is claimed is:

1. A peptide selected from the group consisting of N-Gly-Lys-Arg-Ile-Lys-Gly-Thr-OH (SEQ ID NO: 1), N-Val-Leu-Gly-Lys-Arg-Ile-Lys-Gly-Thr-OH (SEQ ID NO: 2), N-Ile-Glu-Val-Leu-Gly-Lys-Arg-Ile-Lys-Gly-Thr-OH (SEQ ID NO: 3), N-Ile-Asp-Val-Leu-Gly-Lys-Arg-Ile-Lys-Gly-Thr-OH (SEQ ID NO: 4), N-Ile-Arg-Val-Leu-Gly-Lys-Arg-Ile-Lys-Gly-Thr-OH (SEQ ID NO: 5), N-Ile-Glu-Val-Thr-Gly-Lys-Arg-Ile-Lys-Gly-Thr-OH (SEQ ID NO: 6), N-Ile-Asp-Val-Thr-Gly-Lys-Arg-Ile-Lys-Gly-Thr-OH (SEQ ID NO: 7), and N-Ile-Arg-Val-Thr-Gly-Lys-Arg-Ile-Lys-Gly-Thr-OH (SEQ ID NO: 8).

2. The peptide of claim 1, wherein said peptide binds to developmental peptide receptors.

3. A compound comprising the peptide of claim 1 and an agent.

4. The compound of claim 3, wherein said agent is selected from the group consisting of a protein, a lipid and a carbohydrate residue.

5. The compound of claim 3, wherein said agent is a pharmaceutical carrier.

6. A peptide as set forth in SEQ ID NO: 1 (N-Gly-Lys-Arg-Ile-Lys-Gly-Thr-OH).

7. A peptide as set forth in SEQ ID NO: 2 (N-Val-Leu-Gly-Lys-Arg-Ile-Lys-Gly-Thr-OH).

8. A peptide as set forth in SEQ ID NO: 3 (N-Ile-Glu-Val-Leu-Gly-Lys-Arg-Ile-Lys-Gly-Thr-OH).

9. A peptide as set forth in SEQ ID NO: 4 (N-Ile-Asp-Val-Leu-Gly-Lys-Arg-Ile-Lys-Gly-Thr-OH).

10. A peptide as set forth in SEQ ID NO: 5 (N-Ile-Arg-Val-Leu-Gly-Lys-Arg-Ile-Lys-Gly-Thr-OH).

11. A peptide as set forth in SEQ ID NO: 6 (N-Ile-Glu-Val-Thr-Gly-Lys-Arg-Ile-Lys-Gly-Thr-OH).

12. A peptide as set forth in SEQ ID NO: 7 (N-Ile-Asp-Val-Thr-Gly-Lys-Arg-Ile Lys-Gly-Thr-OH).

13. A peptide as set forth in SEQ ID NO: 8 (N-Ile-Arg-Val-Thr-Gly-Lys-Arg-Ile-Lys-Gly-Thr-OH).

* * * * *

SEQUENCE LISTING

<160> NUMBER OF SEQ ID NOS: 9

<210> SEQ ID NO 1
<211> LENGTH: 7
<212> TYPE: PRT
<213> ORGANISM: Homo sapiens

<400> SEQUENCE: 1

Gly Lys Arg Ile Lys Gly Thr
1               5

<210> SEQ ID NO 2
<211> LENGTH: 9
<212> TYPE: PRT
<213> ORGANISM: Homo sapiens

<400> SEQUENCE: 2

Val Leu Gly Lys Arg Ile Lys Gly Thr
1               5

<210> SEQ ID NO 3
<211> LENGTH: 11
<212> TYPE: PRT
<213> ORGANISM: Homo sapiens

<400> SEQUENCE: 3

Ile Glu Val Leu Gly Lys Arg Ile Lys Gly Thr
1               5                   10

<210> SEQ ID NO 4
<211> LENGTH: 11
<212> TYPE: PRT
<213> ORGANISM: Homo sapiens

<400> SEQUENCE: 4

Ile Asp Val Leu Gly Lys Arg Ile Lys Gly Thr
1               5                   10

<210> SEQ ID NO 5
<211> LENGTH: 11
<212> TYPE: PRT
<213> ORGANISM: Homo sapiens

<400> SEQUENCE: 5

Ile Arg Val Leu Gly Lys Arg Ile Lys Gly Thr
1               5                   10

<210> SEQ ID NO 6
<211> LENGTH: 11
<212> TYPE: PRT
<213> ORGANISM: Homo sapiens

<400> SEQUENCE: 6

Ile Glu Val Thr Gly Lys Arg Ile Lys Gly Thr
1               5                   10

<210> SEQ ID NO 7
<211> LENGTH: 11
<212> TYPE: PRT
<213> ORGANISM: Homo sapiens

<400> SEQUENCE: 7

Ile Asp Val Thr Gly Lys Arg Ile Lys Gly Thr

```
                    1               5                   10

<210> SEQ ID NO 8
<211> LENGTH: 11
<212> TYPE: PRT
<213> ORGANISM: Homo sapiens

<400> SEQUENCE: 8

Ile Arg Val Thr Gly Lys Arg Ile Lys Gly Thr
1               5                   10

<210> SEQ ID NO 9
<211> LENGTH: 4
<212> TYPE: PRT
<213> ORGANISM: Homo sapiens

<400> SEQUENCE: 9

Gly Lys Arg Ile
1
```